United States Patent [19]

Failli et al.

[11] Patent Number: 5,159,085
[45] Date of Patent: Oct. 27, 1992

[54] 2-ANILINO PHENYLACETIC ACID DERIVATIVES AS INHIBITORS OF $PLA_2$ AND LIPOXYGENASE

[75] Inventors: Amedeo A. Failli, Princeton Junction, N.J.; Anthony F. Kreft, III, Trooper; John H. Musser, Yardley, both of Pa.

[73] Assignee: American Home Products Corporation, New York, N.Y.

[21] Appl. No.: 667,732

[22] Filed: Apr. 4, 1991

Related U.S. Application Data

[62] Division of Ser. No. 428,092, Oct. 27, 1989, Pat. No. 5,021,576.

[51] Int. Cl.$^5$ .......................................... C07D 235/04
[52] U.S. Cl. ............................ 548/310.1; 548/341.1; 548/342.5
[58] Field of Search .................... 548/486, 330, 333

[56] References Cited

U.S. PATENT DOCUMENTS 4,772,703  9/1988  Musser et al. ................... 548/330

OTHER PUBLICATIONS

CA 114:61703a Preparation of Cycloxygenase-... Hydroxamates, Sallman, Dec. 1985.
CA 78:58069f Antiinflammatory ... Acid Derivatives, Boissier et al., Oct. 1968, p. 489.
CA 94:15406b Phenylalkanoic Acid ... Containing Them, Ueda et al., Feb. 1980, p. 409.

*Primary Examiner*—Mary C. Lee
*Assistant Examiner*—Joseph K. McKane
*Attorney, Agent, or Firm*—George Tarnowski

[57] ABSTRACT

There are disclosed compounds of the formula

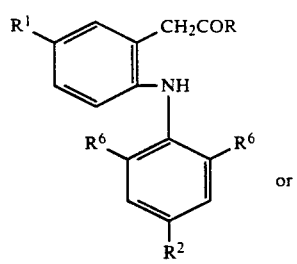

or

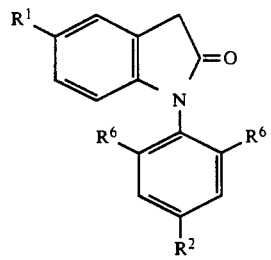

wherein
R is hydroxy, lower alkoxy or lower alkoxyamino;
$R^1$ is hydrogen or $A(CH_2)_nO$—;
$R^2$ is hydrogen or $A(CH_2)_nO$—, with the proviso that one of $R^1$ and $R^2$ is hydrogen;
n is 1-2;
A is phenoxyethyl, phenoxyphenyl or a group having the formula

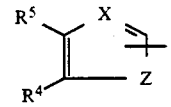

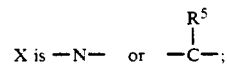

X is —N— or —C—;

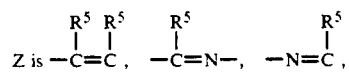

Z is —C=C, —C=N—, —N=C,

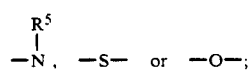

—N, —S— or —O—;

$R^3$ is hydrogen, lower alkyl or phenyl;
$R^4$ is hydrogen or lower alkyl; or
$R^3$ and $R^4$ taken together form a benzene ring;
$R^5$ is hydrogen or lower alkyl;
$R^6$ is hydrogen, halo or lower alkyl;

and the pharmacologically acceptable salts thereof, and their use in the treatment of inflammatory conditions, such as rheumatoid arthritis, ulcerative colitis, psoriasis and other immediate hypersensitivity reactions; in the treatment of leukotriene-mediated naso-bronchial obstructive air-passageway conditions, such as allergic rhinitis, allergic bronchial asthma and the like; and as gastic cytoprotective agents.

3 Claims, No Drawings

2-ANILINO PHENYLACETIC ACID DERIVATIVES AS INHIBITORS OF PLA$_2$ AND LIPOXYGENASE

This is a division of application Ser. No. 07/428,092 filed Oct. 27, 1989 now U.S. Pat. No. 5,021,576.

This invention relates to novel 2-anilinophenylacetic acid derivatives possessing lipoxygenase inhibitory, phospholipase A$_2$ inhibitory and leukotriene antagonist activity, which are useful as anti-inflammatory, antiallergic and cytoprotective agents.

It is now well-established that arachidonic acid (AA) is metabolized in mammals by two distinct pathways. The metabolism of arachidonic acid by cyclooxygenase enzymes results in the production of prostaglandins and thromboxanes. The physiological activity of the prostaglandins has already been amply elucidated in recent years. It is now known that prostaglandins arise from the endoperoxides PGG$_2$ and PGH$_2$ by the cyclooxygenase pathway of arachidonic acid metabolism. These endoperoxides are also the precursors of the thromboxanes (Tx) A$_2$ and B$_2$. TxA$_2$ is a vasoconstrictor which stimulates platelet aggregation. In the normal situation, the vasoconstrictive and platelet aggregating properties of the thromboxanes are balanced by another product arising from the endoperoxides in the cyclooxygenase pathway, prostacyclin (PGI$_2$), which is a vasodilator with platelet aggregation inhibitory activity. In the event prostacyclin synthesis is impaired and/or platelet activation is enhanced, then thrombosis and vasoconstriction is favored. The role of prostanoids in haemostasis and thrombosis are reviewed by R. J. Gryglewski, *CRC Crit. Rev. Biochem.*, 7, 291 (1980) and J. B. Smith, *Am. J. Pathol.*, 99, 743 (1980). Cyclooxygenase metabolites are known to participate directly in the inflammatory response [see Higgs et al., Annals of Clinical Research, 16, 287-299 (1984)]. This is through their vasodepressor activities, participation in pain and fever augmentation of peptide mediator vascular permeability and edema forming properties. Finally, various aspects of cell mediated immunity are influenced by cyclooxygenase products.

The other pathway of AA metabolism involves lipoxygenase enzymes and results in the production of a number of oxidative products called leukotrienes. The latter are designated by the LT nomenclature system, and the most significant products of the lipoxygenase metabolic pathway are the leukotrienes B$_4$, C$_4$ and D$_4$. The substance denominated slow-reacting substance of anaphylaxis (SRS-A) has been shown to consist of a mixture of leukotrienes, with LTC$_4$ and LTD$_4$ as the primary products and having varying amounts of other leukotriene metabolites [see Bach et al., *J. Immun.*, 215, 115-118 (1980); *Biochem. Biophys. Res. Commun.*, 93, 1121-1126 (1980)].

The significance of these leukotrienes is that a great deal of evidence has been accumulated showing that leukotrienes participate in inflammatory reactions, exhibit chemotactic activities, stimulate lysosomal enzyme release and act as important factors in the immediate hypersensitivity reaction. It has been shown that LTC$_4$ and LTD$_4$ are potent bronchoconstrictors of the human bronchi [see Dahlen et al., *Nature*, 288, 484-486 (1980) and Piper, *Int. Arch. Appl. Immunol.*, 76, suppl. 1, 43 (1985)] which stimulate the release of mucus from airways in vitro [Marom et al., *Am. Rev. Resp. Dis.*, 126, 449 (1982)], are potent vasodilators in skin [see Bisgaard et al., *Prostaglandins*, 23, 797 (1982)], and produce a wheal and flare response [Camp et al., *Br. J. Pharmacol.*, 80, 497 (1983)]. The nonpeptide leukotriene, LTB$_4$, is a powerful chemotactic factor for leukocytes [see A. W. Ford-Hutchinson, *J. Roy. Soc. Med.*, 74, 831-833 (1981)], which stimulates cell accumulation and affects vascular smooth muscle [see Bray, *Br. Med. Bull.*, 39, 249 (1983)]. The activity of leukotrienes as mediators of inflammation and hypersensitivity is extensively reviewed in Bailey and Casey, *Ann. Reports Med. Chem.*, 17, 203-217 (1982) and in Bray, *Agents and Actions*, 19, 87 (1986).

Phospholipase A$_2$ (PLA$_2$) is the critical rate limiting enzyme in the arachidonic acid (AA) cascade since it is responsible for the hydrolysis of esterified AA from the C-2 position of membrane phospholipids. This reaction generates two products (1) free AA which is then available for subsequent metabolism by either the cyclooxygenase or lipoxygenase enzymes and (2) lysophospholipid. When alkyl-arachidonoyl-glycerophosphatidylcholine is acted upon by the PLA$_2$ the generation of platelet activating factor (PAF) is initiated; PAF is pro-inflammatory in its own right [see Wedmore et al., *Br. J. Pharmacol.*, 74, 916-917 (1981)]. In this regard it may be noted that the anti-inflammatory steroids are thought to inhibit eicosanoid synthesis by inducing the synthesis of a PLA$_2$ inhibitory protein denominated macrocortin or lipomodulin [see Flower et al., *Nature*, London, 278, 456 (1979) and Hirata et al., *Proc. Natn. Acad. Sci. U.S.A.*, 77, 2533 (1980)].

As the initial step leading to subsequent conversion of AA to the various eicosanoids by the cyclooxygenase and lipoxygenase pathways, the PLA$_2$-mediated release of AA from membrane phospholipids is a critical event in attempting to deal with the various physiological manifestations which are based on the activity of the eicosanoids and/or PAF. Thus, while PLA$_2$ has been shown to be required for platelet aggregation [Pickett et al., *Biochem. J.*, 160, 405 (1976)], cardiac contraction and excitation [Geisler et al., *Pharm. Res. Commun.*, 9, 117 (1977)], as well as prostaglandin synthesis [Vogt, *Adv. Prostagl. Thromb. Res.*, 3, 89 (1978)], the inhibition of PLA$_2$ is indicated in the therapeutic treatment of both PAF induced or cyclooxygenase and/or lipoxygenase pathway product-mediated physiological conditions.

There is also evidence that products of the cyclooxygenase/lipoxygenase pathways play key roles in both the pathogenesis of gastric mucosal damage due to extracellular (gastric and intestinal contents, microorganisms, and the like) or intracellular (ischemia, viruses, etc.) agents, as well as in cytoprotection against such damage. Thus, on the one hand prostaglandins exert a cytoprotective effect on the gastric mucosa [see Robert, *Gastroenterology*, 77, 761-767 (1979)] and this action of the prostaglandins, especially of the E series, is considered to be of importance in the treatment of gastrointestinal ulceration [see Isselbacher, *Drugs*, 33 (suppl.), 38-46 (1987)]. On the other hand, ex vivo experiments have shown that gastric mucosal tissue from ethanolpretreated rats is capable of LTC$_4$ generation and that this LTC$_4$ production is quantitatively related to the severity of the ethanol damage [see Lange et al., *Naunyn-Schmiedeberg's Arch. Pharmacol. Suppl.*, 330, R27, (1985)]. It has also been demonstrated that LTC$_4$ can induce vasoconstriction in both venous and arteriolar vessels in the rat submucosa [see Whittle, *IUPHAR Ninth Int. Cong. of Pharm.*, S30-2, London, England (1984)]. This is significant since ethanol-induced lesion formation in gastric mucosa may be multifactorial with, for example, stasis of gastric blood flow contributing significantly to the development of the hemorrhagic necrotic aspects of the tissue injury [see Guth et al., *Gastroenterology*, 87, 1083-90 (1984)]. Moreover, in the anesthetized cat, exogenous $LTD_4$ evokes both increased pepsin secretion and decreased transgastric potential [Pendleton et al., *Eur. J. Pharmacol.*, 125, 297-99 (1986)]. A particularly significant recent finding in this regard is that 5-lipoxygenase inhibitors and some leukotriene antagonists protect the gastric mucosa against lesions induced by the oral or parenteral administration of most nonsteroidal anti-inflammatory drugs [see Rainsford, *Agents and Actions*, 21, 316-19 (1987)]. Platelet activating factor (PAF) is also implicated as a mediator of gastrointestinal damage, and it has been recently shown that 5-lipoxygenase inhibitors inhibit PAF-induced gastric mucosal damage (*Gastroenterology*, 96, A55, A434, 1989). Accordingly, a significant body of evidence implicates the involvement of lipoxygenase products in the development of pathological features associated with gastric mucosal lesions, such as for example, those induced by ethanol exposure and administration of non-steroidal anti-inflammatory drugs. Thus, compounds which inhibit the biological effects of leukotrienes and PAF and/or which control the biosynthesis of these substances, as by inhibiting 5-lipoxygenase, are considered to be of value as cytoprotective agents.

Accordingly, the biological activity of the leukotrienes and SRS's, and of lipoxygenase as the enzyme leading to the metabolism of AA to leukotrienes, indicates that a rational approach to drug therapy to prevent, remove or ameliorate the symptoms of allergies, anaphylaxis, asthma and inflammation and for gastric cytoprotection must focus on either blocking the release of mediators of these conditions or antagonizing their effects. Thus, compounds which inhibit the biological effects of the leukotrienes and SRS's and/or which control the biosynthesis of these substances, as by inhibiting the $PLA_2$-mediated release of arachidonic acid from membrane phospholipids, or by inhibiting lipoxygenase, are considered to be of value in treating such conditions as allergic bronchial asthma, allergic rhinitis, as well as in other immediate hypersensitivity reactions and in providing gastric cytoprotection.

It has now been found that certain novel 2-anilinophenylacetic acid derivatives inhibit $PLA_2$ and lipoxygenase, and antagonize products of the lipoxygenase pathway, and so are useful as anti-inflammatory, antiallergic and cytoprotective agents. The present invention provides novel compounds having the following formula:

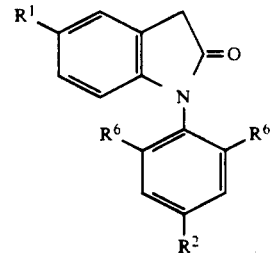

or

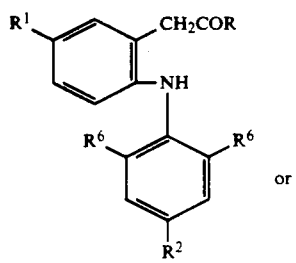

wherein
R is hydroxy, lower alkoxy or lower alkoxyamino;
$R^1$ is hydrogen or $A(CH_2)_nO-$;
$R^2$ is hydrogen or $A(CH_2)_nO-$, with the proviso that one of $R^1$ and $R^2$ is hydrogen;
n is 1-2;
A is phenoxyethyl, phenoxyphenyl or a group having the formula

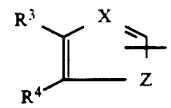

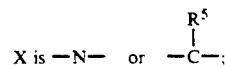

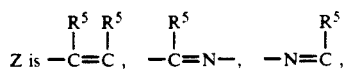

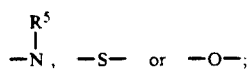

$R^3$ is hydrogen, lower alkyl or phenyl;
$R^4$ is hydrogen or lower alkyl; or
$R^3$ and $R^4$ taken together form a benzene ring;
$R^5$ is hydrogen or lower alkyl;
$R^6$ is hydrogen, halo or lower alkyl;
and the pharmacologically acceptable salts thereof.

The terms "lower alkoxy", "lower alkoxyamino" and "lower alkyl" refer to moieties having 1-6 carbon atoms in the carbon chain. The term "halo" refers to fluoro, chloro or bromo.

The grouping A embraces, inter alia, 5- or 6-membered unsaturated nitrogen, sulfur or oxygen containing mono- or benzofused-heterocycles, optionally substituted with lower alkyl or phenyl. The foregoing definition embraces the following heterocyclic moieties: furyl, pyrrolyl, thienyl, oxazolyl, thiazolyl, imidazolyl, pyridyl, pyrazinyl, pyrimidinyl, benzofuranyl, benzothienyl, benzothiazolyl, indolyl, benzoxazolyl, quinolinyl, quinazolinyl, benzimidazolyl, quinoxalinyl, quinazolinyl and the like. Especially preferred are quinolinyl, benzothiazolyl, and benzimidazolyl.

The compounds of the invention can form pharmacologically acceptable salts from pharmacologically acceptable organic and inorganic acids such as hydrochloric, hydrobromic, sulfonic, sulfuric, phosphoric, nitric, maleic, fumaric, benzoic, ascorbic, pamoic, succinic, methanesulfonic, acetic, propionic, tartaric, citric, lactic, malic, mandelic, cinnamic, palmitic, itaconic and benzenesulfonic. The compounds which are carboxylic acids are capable of forming alkali metal and alkaline earth carboxylates and carboxylates of pharmacologically acceptable cations derived from ammonia or a basic amine. Examples of the latter include but are not limited to cations such as ammonium, mono-, di-, and trimethylammonium, mono-, di- and triethylammonium, mono-, di- and tripropylammonium (iso and normal), ethyldimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butyl-piperidinium, 2-methylpiperidinium, 1-ethyl-2-methylpiperidinium, mono-, di- and triethanolammonium, ethyl diethanolammonium, n-butylmonoethanolammonium, tris(hydroxymethyl)methylammonium, phenylmonoethanolammonium, and the like.

The compounds of the invention can be prepared by the following reaction schemes. When it is desired to prepare compounds having the formula

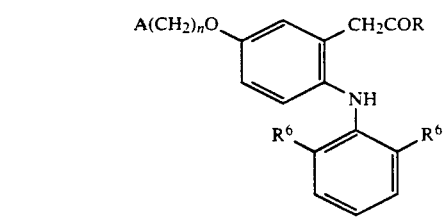

a 2.6-dialkyl or 2,6-dihaloaniline (such as 2,6-dichloroaniline) is reacted with acetyl chloride followed by reaction with 4-bromoanisole to yield the intermediate N-(4-methoxyphenyl)-2,6-dichloro aniline:

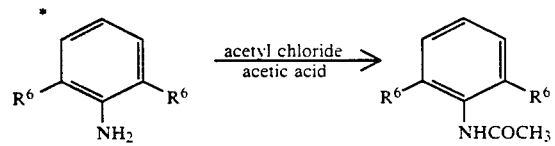

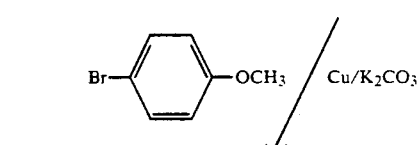

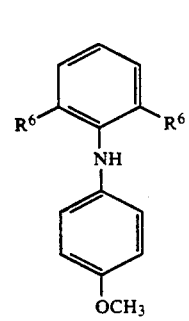

*One may also start with 2.6-dialkyl or 2,6-dihalo anilines.

The latter intermediate is reacted with chloroacetyl chloride followed by ring closure in the presence of aluminum chloride to yield a substituted 2-indolinone intermediate:

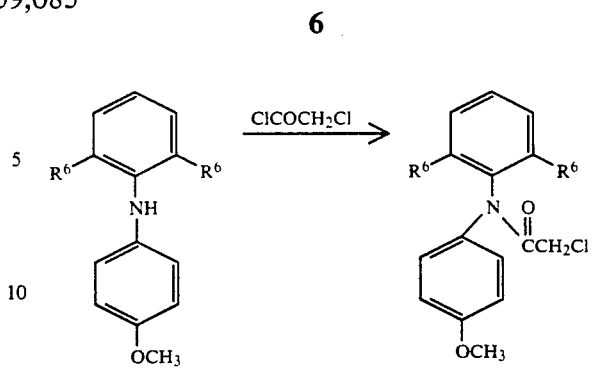

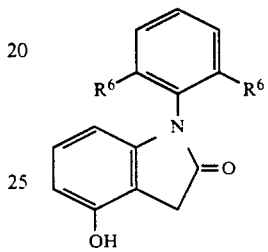

The latter 2-indolinone intermediate is subjected to ring opening, esterification of the carboxylic acid followed by reaction with an appropriate haloalkyl A group, where A is as defined hereinbefore:

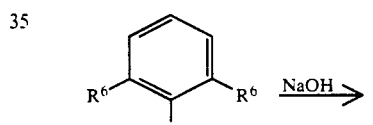

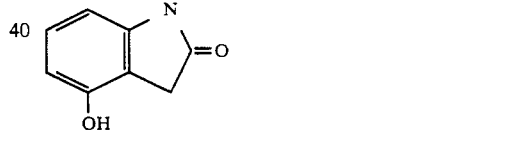

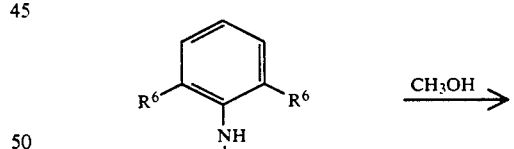

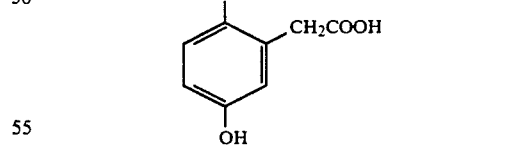

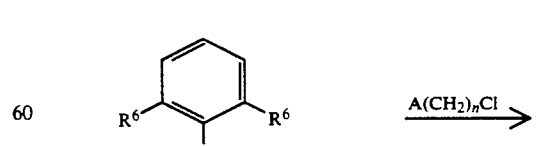

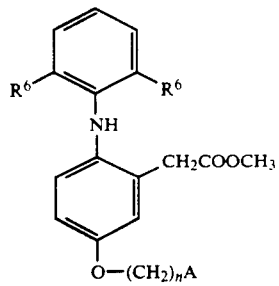

In the above sequence, where $R^6$ represents bromo or chloro groups, the latter can be removed to yield mono- or des- $R^6$ compounds by subjecting the 2-indolinone intermediate or its open ring form to treatment with 5% Pd/C $H_2$ at atmospheric or greater pressure. The resulting intermediate is then treated as outlined above, i.e. esterification and reaction with the intermediate, A-$(CH_2)_nCl$. The final product ester can be further hydrolyzed to yield the free acid, which in turn can be converted to the desired pharmacologically acceptable salt by conventional methods.

When it is desired to prepare compounds having the formula

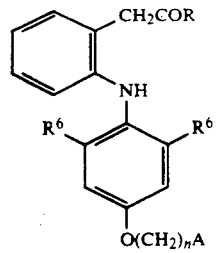

the following reaction scheme can be employed:

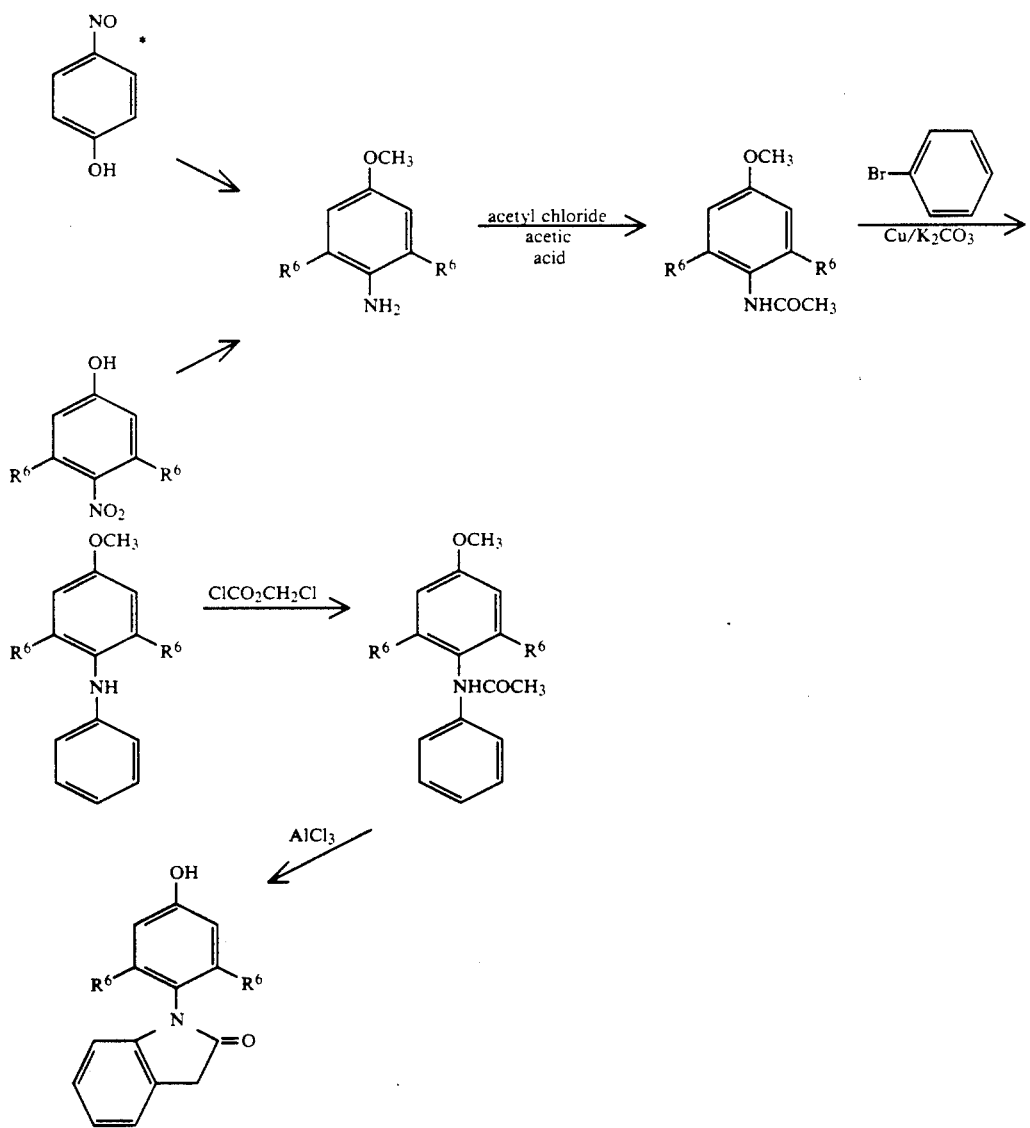

-continued

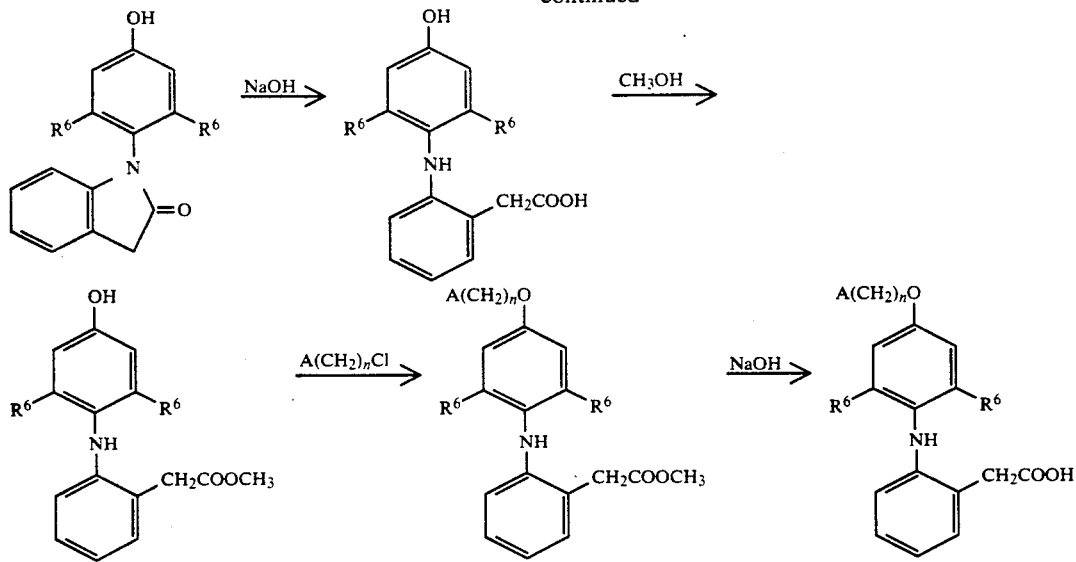

*The starting material p-nitrophenol, when subjected to treatment with methanol and toluene saturated with hydrogen chloride, yields the intermediate 2,5-disubstituted-4-methoxyaniline in which the 2,5-disubstituents are chloro groups.

Similarly to the first reaction sequence discussed supra, where $R^6$ represents chloro or bromo groups, the latter can be partially or totally removed by treatment with 5% Pd/C $H_2$ to yield the mono- or des- $R^6$ compounds. As indicated earlier, the final product free acid can be converted by known means to the desired pharmacologically acceptable salts.

The starting materials used in the reaction sequences outlined above are available commercially or can be prepared by known methods conventional in the art. Thus, for example, the intermediate compound 2-bromomethyl-7-chloroquinoline can be prepared by the following reaction sequence:

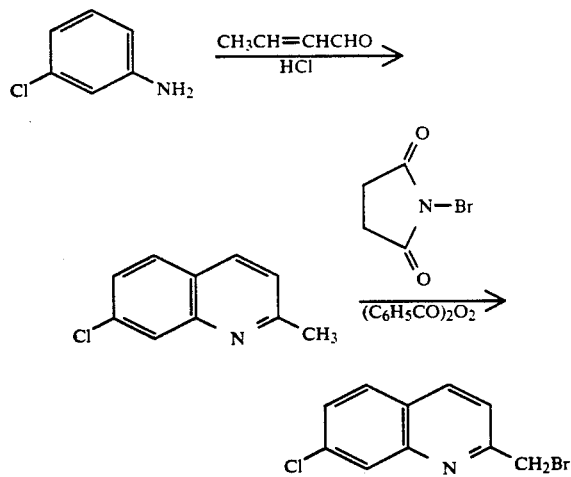

The compounds of the invention, by virtue of their ability to inhibit the activity of $PLA_2$ enzyme, as well as that of lipoxygenase enzyme and to antagonize mediators arising from the enzymatic pathway, are useful in the treatment of conditions mediated by products of the oxidation of arachidonic acid. Accordingly, the compounds are indicated in the treatment of such diseases as rheumatoid arthritis, inflammatory bowel disease, osteoarthritis, tendinitis, bursitis, psoriasis (and related skin inflammation) and similar conditions involving inflammation. Moreover, by virtue of their ability to inhibit the activity of lipoxygenase enzyme and by their ability to antagonize the effect of $LTC_4$, $LTD_4$ and $LTE_4$, which are the constituents of SRS-A, they are useful for the inhibition of symptoms induced by these leukotrienes. Accordingly, the compounds are indicated in the prevention and treatment of those disease states in which $LTC_4$, $LTD_4$ and $LTE_4$ are causative factors, for example allergic rhinitis, allergic bronchial asthma and other leukotriene mediated naso-bronchial obstructive air-passageway conditions, as well as in other immediate hypersensitivity reactions, such as allergic conjunctivitis. The compounds are especially valuable in the prevention and treatment of allegic bronchial asthma.

The compounds of the invention are cytoprotective agents and are considered especially useful when administered with conventional non-steroidal anti-inflammatory drugs, whose major side effect is gastrointestinal irritation. The cytoprotective effect of the compounds of the invention significantly reduces the gastroirritant impact of conventional anti-inflammatory drugs. This effect is based not only on the ability of the compounds of the invention to inhibit the biological effects of leukotrienes and/or control the biosynthesis of these substances, as by inhibiting lipoxygenase, but also by a shunting effect, whereby the control of the lipoxygenase pathway "shunts" the oxidation of arachidonic acid into the cyclooxygenase pathway, giving rise to an increase in the formation of cytoprotective prostaglandins. These biological effects make the compounds of the invention especially useful in treating such conditions as erosive esophagitis, inflammatory bowel disease and induced hemorrhagic lesions such as those induced by alcohol or non-steroidal anti-inflammatory drugs (NSAID's), hepatic ischemia, noxious agent induced damage or necrosis of hepatic, pancreatic, renal or myocardial tissue; liver parenchymal damage caused by hepatotoxic agents such as carbon tetrachloride and D-galactosamine; ischemic renal failure; disease-induced hepatic damage; bile salt-induced pancreatic or gastric damage; trauma or stress-induced cell damage; and glycerol-induced renal failure.

When the compounds of the invention are employed in the treatment of allergic airway disorders, as anti-inflammatory agents and/or as cytoprotective agents, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto on oral administration. The compounds may also be injected parenterally, in which case they are used in the form of a sterile solution containing other solutes, for example, enough saline or glucose to make the solution isotonic. For administration by inhalation or insufflation, the compounds may be formulated into an aqueous or partially aqueous solution, which can then be utilized in the form of an aerosol.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration that will generally afford effective results without causing any harmful or deleterious side effects, and can be administered either as a single unit dose, or if desired, the dosage may be divided into convenient subunits administered at suitable times throughout the day.

The $PLA_2$ and lipoxygenase inhibitory and leukotriene antagonist effects, as well as the anti-inflammatory and potential gastroirritant effects of the compounds of the invention, may be demonstrated by standard pharmacological procedures which are described more fully in the examples given hereinafter.

These procedures, inter alia, determine the specificity of action of the compounds of the invention as $PLA_2$ inhibitors as measured by their ability to inhibit the synthesis of $LTB_4$ and $TxB_2$ by rat glycogen-elicited polymorphonuclear leukocytes, as well as measure their ability to inhibit arachidonic acid release mediated by human and non-human source $PLA_2$. The procedures further measure the ability of the compounds of the invention to inhibit, in vivo, the activity of exogenously administered $PLA_2$. The pharmacological testing additionally demonstrates the ability of the compounds of the invention to inhibit, in vivo, the lipoxygenase and cyclooxygenase pathways of arachidonic acid metabolism; the in vitro leukotriene antagonist activity of the compounds of the invention; and also measures the in vivo activity of the compounds as anti-inflammatory agents in the rat carrageenan paw edema assay. Finally, the potential of the compounds to induce acute gastroirritation in rats is measured in a test procedure.

The following examples show the preparation and pharmacological testing of compounds within the invention.

EXAMPLE 1

2-[(2,6-Dichlorophenyl)amino]-5-(2-quinolinylmethoxy)-benzene acetic acid methyl ester ethanedioate (1:1)

A. 2,6-Dichloroacetanilide

To a mechanically stirred solution of 2,6-dichloroaniline (76 g, 0.047 mol) in 60 mL of glacial acetic acid is added dropwise acetyl chloride (36 mL, 0.5 mol). After the addition is complete, the reaction mixture is heated at 90° C. for 20 minutes. The solution is poured into ice water (500 mL), forming a white precipitate. The solids are filtered, washed with water and dried to give the product (91.8 g, 96%, white solid, m.p. 179°-180° C., lit. m.p. 180°-181° C. form glacial acetic acid).

NMR ($CDCl_3$, 200 MHz): δ 2.22 (s, 3H, $CH_3CO$), 7.06 (broad, 1H, NH), 7.14–7.45 (m, 3H, ArH).

B. N-(4-methoxyphenyl)-2,6-dichloroaniline

Under a nitrogen atmosphere, a mixture of 2,6-dichloroacetanilide (3.0 g, 15.6 mmol), potassium carbonate (1.08 g, 7.8 mmol), copper powder (0.1 g), and 30 mL of 4-bromoanisole is heated at reflux for 6 hours. The reaction mixture is steam distilled* to remove the excess anisole. The residue is partitioned with ethyl ether and water (30 mL each). The organic phase is washed with brine (30 mL) and dried ($MgSO_4$). Removal of the solvent affords 3.9 g of the intermediate N-(4-methoxyphenyl)-2,6-dichloro acetanilide as an amber oil. The crude intermediate is refluxed for 6 hours in 20 mL of 10% ethanolic KOH. The solvent is evaporated and the residue diluted with water (50 mL). The solids are filtered, washed with water and dried under high vacuum (over $P_2O_5$) to give the title product (2.9 g, 69%, brown oil, m.p. lit: 75°-77° C. from chloroform).

* In place of steam distillation, the excess anisole may be removed by repeated evaporation of water from the crude product mixture until no more anisole can be detected in the azeotrope.

NMR ($CDCl_3$, 400 MHz): δ3.77 (s, 3H, $OCH_3$), 5.76 (broad, 1H, NH), 6.73 (d, J=9 Hz, 2H, ArH), 6.81 (d, J=9 Hz, 2H, ArH), 6.96 (t, J=8 Hz, 1H, ArH), 7.33 (d, J=8 Hz, 2H, ArH).

MS (EI, m/z): 267 ($M^+$); 252 ($M-CH_3^+$, b.p.); 216, 188, 154.

C. N-(2,6-dichlorophenyl)-N-(4-methoxyphenyl)-chloroacetamide

Under anhydrous conditions, a mixture of N-(4-methoxyphenyl)-2,6-dichloroaniline (20.2 g, 75.4 mmmol) in 175 mL of chloroacetyl chloride is heated at reflux for 1 hour. The excess acid chloride is evaporated in vacuo and the residue partitioned between saturated $NaHCO_3$ solution and ethyl acetate (30 mL each). The organic phase is washed with brine (30 mL) and dried ($Na_2SO_4$). Removal of solvent affords an amber oil. Crystallization of the crude oil from methanol affords the title product (16.63 g, 64%, white needles, m.p. 105°-106° C., lit: 127°-128° C. from methanol) as a 1:1 mixture of rotamers.

NMR ($CDCl_3$, 400 MHz): δ3.78 and 3.81 (2s, 3H, $OCH_3$), 3.96 (s, 1H, $COCH_2Cl$), 4.16 (s, 1H, $COCH_2Cl$), 6.85 (d, 1H, ArH), 6.90 (d, 1H, ArH), 7.19–7.57 (m, 5H, ArH).

MS (EI, m/z): 343 ($M^+$); 308 $(M-Cl)^+$; 252 (b.p.).

Analysis for: $C_{15}H_{12}Cl_3NO_2$. Calculated: C, 52.28; H, 3.51; N, 4.06. Found: C, 51.90; H, 3.76; N, 4.03.

D. 1-(2,6-dichlorophenyl)-5-hydroxy-2-indolinone

Under an atmosphere of nitrogen, a well blended mixture of N-(2,6-dichlorophenyl)-N-(4-methoxyphenyl)chloroacetamide (10 g, 29 mmol) and aluminum chloride (10 g) is heated to 190° C. when mechanical stirring is started. The mixture is heated to 250° C. for 15 minutes and then allowed to cool and kept at 160° C. for another hour. The cool brown solid mass is treated with water (500 mL). The mixture is extracted with 500 mL of ethyl acetate. The organic phase is washed with brine and dried (MgSO$_4$). Removal of solvent affords the product (7.6 g, brown solid, $\geq$95% pure by NMR; lit m.p. 204°-205° C. from methanol-benzene).

NMR (CDCl$_3$, 400 MHz): $\delta$3.74 (s, 2H, CH$_2$CO), 4.70 (broad, 1H, OH), 6.26 (d, 1H, J=8.3 Hz, ArH), 6.66 (dd, 1H, J=8.5 Hz, ArH), 6.88 (s, 1H, ArH), 7.36 (t, 1H, J=8.3 Hz, ArH), 7.49 (d, 2H, J=7.9 H, ArH).

MS (EI, m/z): 293 (M)$^+$; 258 (M-Cl)$^+$; 230 (b.p.).

E. 2-[(2,6-dichlorophenyl)amino]-5-hydroxy benzene acetic acid

A solution of 1-(2,6-dichlorophenyl)-5-hydroxy-2-indolinone (2.0 g, 6.8 mmol) in 25 mL of 2.5N NaOH is heated at reflux for 2 hours. The cool reaction mixture is diluted with 20 mL of water and washed with ethyl ether. The basic layer is acidified with concentrated HCl and extracted with ethyl acetate (2$\times$25 mL). The organic phase is washed with brine and dried (Na$_2$SO$_4$). Removal of solvent affords the product (2.0 g, 95%) as a brown foam (of suitable purity for use in the next step).

NMR (DMSO-d$_6$, 300 MHz): $\delta$3.61 (s, 2H, C-CH$_2$COOH), 6.26 (d, 1H, ArH), 6.48 (dd, 1H, ArH), 6.70 (d, 1H, ArH), 6.71 (s, 1H, NH), 7.06 (m, 1H, ArH), 7.435 (d, 2H, ArH), 9.04 (s, 1H, OH).

MS (EI, m/z): 311/313 (M)$^+$; 293, 137 (b.p.).

F. Methyl-2-[(2,6-dichlorophenyl)amino]-5-hydroxy benzene acetate

A solution of the acid of Step E, above (2.0 g, 6.4 mmol) in 20 mL of methanol containing a few mg of p-toluene sulfonic acid monohydrate is heated at reflux for 3 hours. The solvent is evaporated in vacuo and the residue dissolved in ethyl acetate. The organic phase is washed with saturated NaHCO$_3$, brine and dried (MgSO$_4$). Removal of solvent affords the product (1.9 g, 90%) as a brown foam. It is used as such in the next step.

NMR (DMSO-d$_6$, 400 MHz): $\delta$3.63 (s, 3H, COOCH$_3$), 3.72 (s, 2H, CCH$_2$COO), 6.26 (d, J=8.5 Hz, 1H, ArH), 6.50 (dd, 1H, ArH), 6.58 (s, 1H, NH), 6.65 (d, J=2.79 Hz, 1H, ArH), 7.03 (t, J=8 Hz, 1H, ArH), 7.43 (d, J=8.04 Hz, 2H, ArH).

MS (EI, m/z): 325 (M)$^+$, 230 (b.p.).

G. 2-[(2,6-Dichlorophenyl)amino]-5-(2-quinolinylmethoxy)benzene acetic acid methyl ester Under an atmosphere of nitrogen, a mixture of the crude phenol of Step F, above (5.0 g, 15.4 mmol), potassium carbonate (1.3 g, 9.8 mmol), 18-crown-6 (130 mg), and 2-chloromethyl quinoline (4.1 g, 23 mmol) in 50 mL of acetonitrile is stirred at 60° C. for 24 hours (TLC, silica, dichloromethane-MeOH 19:1). The solvent is evaporated and the residue partitioned between ethyl acetate and water (75 mL each). The insolubles are filtered, the layers separated and the organic phase washed with 1N NaOH and brine. After drying (MgSO$_4$) the solvent is removed in vacuo to give 7.0 g of a thick brown oil. The crude product is purified by flash chromatography (silica Merck 60, dichloromethane and dichloromethane-ethyl acetate 19:1) to give the product (4.2 g, clear oil). The oil is triturated with ethanol to give crystalline product (3.98 g, 55.5%, m.p. 90°-91° C., white solid).

NMR (DMSO-d$_6$, 400 MHz): $\delta$3.62 (s, 3H, COOCH$_3$), 3.79 (s, 2H, C-CH$_2$—COO), 5.27 (s, 2H, OCH$_2$Ar), 6.3 (d, 1H, ArH), 6.76 (s, 1H, NH), 6.82 (dd, 1H, ArH), 7.05 (d, 1H, ArH), 7.09 (t, 1H, J=8.1 Hz, ArH), 7.46 (d, 2H, J=8.1 Hz, ArH), 7.60 (t, 1H, ArH), 7.66 (d, 1H, 8.5 Hz, ArH), 7.76 (t, 1H, ArH), 7.98 (t, 1H, ArH), 8.40 (d, 1H, J=8.47 ArH).

MS (FAB, m/z): 467 (M+H)$^+$, 324, 292, 143 (b.p.).

Analysis for: C$_{25}$H$_{20}$Cl$_2$N$_2$O$_3$. Calculated: C, 64.25; H, 4.31; N, 5.99. Found: C, 64.33; H, 4.37; N, 5.93.

H. 2-[(2,6-Dichlorophenyl)amino]-5-[(2-quinolylmethoxy]benzene acetic acid methyl ester ethanedioate (1:1)

A solution of the compound of Example 1G (2.1 g, 4.5 mmol) in methanol-ethyl acetate (20 mL, 1:1, v/v) is mixed with a solution of oxalic acid (0.405 g, 4.5 mmol) in ether (10 mL). The precipitate is filtered, washed with ether and dried in vacuo to yield the salt (yellow solid, 1.6 g, m.p. 152°-154° C. dec). The salt is recrystallized from ethyl acetate (1.2 g) without change in the m.p.

IR (KBr, cm$^{-1}$): 1730 (CO)

NMR (DMSO-d$_6$, 400 MHz): $\delta$3.62 (s, 3H, OCH$_3$), 3.79 (s, 2H, CCH$_2$COO), 5.27 (s, 2H, OCH$_2$Ar), 6.30 (d, 1H, J=8.74 Hz, ArH), 6.75 (s, 1H, NH), 6.81 (dd, 1H, ArH), 7.01 (d, 1H, J=2.9 Hz, ArH), 7.09 (t, J=8 Hz, 1H, ArH), 7.46 (d, 2H, J=8 Hz, ArH), 7.60 (dt, 1H, ArH), 7.66 (d, 1H, J=8.5 Hz, ArH), 7.77 (dt, 1H, ArH), 7.97-8.01 (m, 2H, ArH), 8.40 (d, 1H, J=8.5 Hz, ArH).

MS (CI, m/z): 471/469/467 (2Cl, b.p., M+H)$^+$, 326, 144

Analysis for: C$_{27}$H$_{22}$Cl$_2$N$_2$O$_7$. Calculated: C, 58.18; H, 3.98; N, 5.03. Found: C, 57.88; H, 4.10; N, 4.80.

EXAMPLE 2

2-[(2,6-Dichlorophenyl)amino]-5-(2-quinolylmethoxy)benzene acetic acid

A solution of the compound of Example 1G (1.1 g, 2.3 mmol) in ethanol (20 mL) and 1N NaOH (10 mL) is stirred at room temperature for 15 minutes. The ethanol is removed (rotovap) and the residue diluted with water and washed with ethyl ether-ethyl acetate 1:1. The mixture is neutralized with 10 mL of 1N HCl (pH 5). The precipitate which forms is filtered, washed with water, and dried to give 0.85 g crude product. Recrystallization from methanol (2 mL) gives pure product (0.68 g, 65%, light yellow solid, m.p. 162° C. sinters, 168° C. melts).

NMR (DMSO-d$_6$, 400 MHz): $\delta$3.69 (s, 2H, CCH$_2$COOH), 5.27 (s, 2H, OCH$_2$Ar), 6.31 (d, 1H, J=8.74 Hz, ArH), 6.81 (dd, 1H, ArH), 6.89 (s, 1H, NH), 7.02 (d, 1H, J=2.84 Hz, ArH), 7.08 (t, 1H, J=8.0 Hz, ArH), 7.45 (d, 2H, J=8.1 Hz, ArH), 7.6 (dt, 1H, ArH), 7.66 (d, 1H, J=8.5 Hz, ArH), 7.77 (dt, 1H, ArH), 7.98 (t, 2H, ArH), 8.40 (d, 1H, J=8.48 Hz, ArH).

MS (FAB, m/z): 453 (M+H)$^+$, 217, 131, 91 (b.p.).

Analysis for: C$_{24}$H$_{18}$Cl$_2$N$_2$O$_3$. Calculated: C, 63.58; H, 4.00; N, 6.18. Found: C, 63.52; H, 3.78; N, 6.15.

EXAMPLE 3

2-[(2,6-Dichlorophenyl)amino]-5-(2-quinolinylmethoxy)benzene acetic acid sodium salt A solution of the compound of Example 1G (0.92 g, 1.97 mmol) in ethanol (20 mL) and 1N NaOH (10 mL) is stirred for one hour at room temperature. The reaction mixture is concentrated in vacuo to a reduced volume. The precipitate which forms is filtered, washed with water and dried over $P_2O_5$ under high vacuum to give the title compound [0.69 g, 73.9%, m.p. (sinters 129° C.) 151° C. melts, off-white solid].

NMR (DMSO-$d_6$, 400 MHz): δ3.32 (s, 2H, CCH$_2$CO), 5.25 (s, 2H, OCH$_2$Ar), 6.18 (d, 1H, J=8.7 Hz, ArH), 6.63 (dd, 1H, ArH), 6.81 (d, 1H, J=2.88 Hz, ArH), 6.97 (t, 1H, J=8 Hz, ArH), 7.38 (d, 2H, J=8 Hz, ArH), 7.57–7.59 (m, 1H, ArH), 7.655 (d, 1H, J=8.5 Hz, ArH), 7.74–7.78 (m, 1H, ArH), 7.96–8.01 (m, 2H, ArH), 8.385 (d, 1H, J=8.5 Hz, ArH), 9.90 (s, 1H, NH).

MS (+FAB, m/z): 475 (M+H)$^+$, 453 (M+H-Na)$^+$.

Analysis for: $C_{24}H_{17}Cl_2NaN_2O_3$. Calculated: C, 60.65; H, 3.60; N, 5.89. Found: C, 60.37; H, 3.59; N, 5.81.

EXAMPLE 4

2-[(2,6-Dichlorophenyl)amino]-5-(2-quinolinylmethoxy)benzene acetic acid 2-amino-2-(hydroxymethyl)-1,3-propanediol salt (1:1)

A solution of the compound of Example 2 (0.80 g, 1.77 mmol) and tris(hydroxymethyl)aminomethane (0.214 g, 1.77 mmol) in 10 mL of acetone-water (1:1, v/v), is concentrated in vacuo. The pale green residue is triturated with ethyl ether overnight. The solids are filtered under an atmosphere of nitrogen (hygroscopic) and dried over $P_2O_5$ to give the title compound (0.72 g, 71%, m.p. 82°–85° C. (dec), yellow solid).

NMR (DMSO-$d_6$, 400 MHz): δ3.39 (s, 6H, CH$_2$OH), 3.43 (s, 2H, CCH$_2$CO), 5.26 (s, 2H, OCH$_2$Ar), 6.23 (d, 1H, J=8.7 Hz, ArH), 6.69 (dd, 1H, ArH), 6.88 (d, 1H, J=2.88 Hz, ArH), 7.00 (t, 1H, J=8 Hz, ArH), 7.40 (d, 2H, J=8 Hz, ArH), 7.57–7.61 (m, 1H, ArH), 7.66 (d, 1H, J=8.5 Hz, ArH), 7.74–7.78 (m, 1H, ArH), 7.98 (m, 2H, ArH), 8.39 (d, 1H, J=8.5 Hz, ArH), 8.88 (broad, 1H, NH).

MS (CI, m/z): δ 456, 454, 453 [(M+H)$^+$, 2Cl], 122 (b.p.)

Analysis for: $C_{28}H_{29}Cl_2N_3O_6 \cdot (1.7\ H_2O)$. Calculated: C, 58.02; H, 5.12; N, 7.27. Found: C, 57.93; H, 5.35; N, 7.12.

EXAMPLE 5

5-[(7-Chloro-2-quinolyl)methoxy]-2-[(2,6-dichlorophenyl)amino]benzene acetic acid methyl ester A. 7-Chloroquinaldine To a solution of m-chloroaniline (25.51 g, 0.2 mol) in 100 mL of 6N HCl kept at reflux is added dropwise with stirring 85% aqueous crotonaldehyde (14.7 g, in 2.6 g of water). After an additional 45 minutes at reflux, the mixture is cooled and extracted with ethyl ether to remove tars. To the vigorously stirred solution is added $ZnCl_2$ (27.2 g, 0.20 mol). A tan gum ball is formed. The mixture is then refluxed for a total of three hours to give a clear brown solution. Upon cooling, a gummy solid is formed which is filtered and triturated with 2-propanol followed by ethyl ether and dried in vacuo to give the quinaldine HCl-ZnCl$_2$ complex. The 7-chloroquinaldine is then isolated by dissolving the complex into 150 mL of water and 50 mL of NH$_4$OH, and concentrated to yield the crude product (tan solid 15.77 g, 44.4%). Purification of the crude product is achieved by flash chromatography, (silica Merck 60, methylene chloride-:ethyl acetate 98:2). Removal of the solvent affords a light tan solid (11.1 g, 31.3%), m.p. dec. 68°–70° C. (lit: 42%, m.p. 75°–77° C.).

NMR (CDCl$_3$, 400 MHz): δ2.73 (s, 3H, CH$_3$), 7.28 (d, 1H, J=8.48 Hz, ArH), 7.44 (dd, 1H, ArH), 7.70 (d, 1H, J=8.66 Hz, ArH), 8.00–8.03 (m, 2H, ArH).

MS (EI, m/z): 177 (b.p., M)$^+$, 142 (M-Cl)$^+$, 162 (M-CH$_3$)$^+$.

B. 2-Bromomethyl-7-chloroquinoline

A stirred suspension of 7-chloroquinaldine (18.0 g, 0.10 mol), N-bromosuccinimide (18.0 g, 0.10 mol), and benzoyl peroxide (1.0 g, 0.004 mol) in CCl$_4$ (400 mL) is illuminated with a 300 W reflector bulb for 6 hours. The reaction mixture is cooled and filtered through a plug of silica using hexane:ethyl acetate (7:3). The yellow filtrate is concentrated to give a crude mixture of unreacted starting material together with the monobromo and less polar dibromo products. The crude material is purified by flash chromatography (preabsorbed on silica Merck 60 with methylene chloride and then eluted with hexane:ethyl acetate 95:5), to yield fairly pure title product as an off-white solid. (17.31 g, 48.9% yield based on recovered starting material, m.p. 111°–112° C.).

NMR (CDCl$_3$, 400 MHz): δ4.68 (s, 2H, CH$_2$Br), 7.51 (dd, 1H, ArH), 7.57 (d, 1H, J=8.55 Hz, ArH), 7.75 (d, 1H, ArH), 8.07–8.26 (m, 2H, ArH).

MS (EI, m/z): 259/257/255 (M$^+$, Br/Cl ratio 1:1).

C. 5-[(7-Chloro-2-quinolyl)methoxy]-2-[(2,6-dichlorophenyl)amino]benzene acetic acid methyl ester To a solution of the compound of Example 1F, (4 g, 12.4 mmol) in acetonitrile (40 mL) is added potassium carbonate (0.945 g, 6.84 mmol), tetrabutylammonium bromide (2 g) and 2-bromomethyl-7-chloroquinoline (3.5 g, 13.64 mmol). The mixture is heated at 60° C. under nitrogen for 48 hours. The solvent is evaporated and the tan residue is partitioned between ethyl acetate and water. The organic layer is dried (Na$_2$SO$_4$) and concentrated to give a brown oil which sets up upon standing (6.75 g). The crude product is purified by flash chromatography (on silica Merck 60, preabsorbed in methylene chloride, eluted with hexane-ethyl acetate 9:1) to provide the title compound as a tan solid (4.43 g, 71.2%). Trituration with methanol (twice) gives off-white solid (4.22 g, 67.8%, m.p. 115°–117° C.).

IR (KBr, cm$^{-1}$): 1745 (CO)

NMR (CDCl$_3$, 400 MHz): δ3.74 (s, 3H, COOCH$_3$), 3.80 (s, 2H, CH$_2$COO), 5.39 (s, 2H, OCH$_2$Ar), 6.53 (d, 1H, J=8.73 Hz, ArH), 6.63 (s, 1H, NH), 6.80 (dd, 1H, ArH), 6.95 (mm, 2H, ArH), 7.31 (d, 2H, J=8.03 Hz, ArH), 7.54 (d, 1H, J=8.54 Hz, ArH), 7.75 (d, 1H, J=8.54 Hz, ArH), 7.80 (d, 1H, J=8.68 Hz, ArH), 8.19 (s, 1H, ArH), 8.25 (d, 1H, J=7.69 Hz, ArH).

MS (EI, m/z): 504/502/500 (M$^+$, 3 Cl), 324, 292 (b.p.) 177.

Analysis for: $C_{25}H_{19}Cl_3N_2O_3$. Calculated: C, 59.84; H, 3.82; N, 5.58. Found: C, 59.63; H, 3.87; N, 5.59.

EXAMPLE 6

5[(7-Chloro-2-quinolinyl)methoxy]-2-[(2,6-dichlorophenyl)amino]benzene acetic acid 1N NaOH (31.7 mL) is added dropwise to a solution of the compound of Example 5 (3.7 g, 7.3 mmol) in ethanol (62 mL) and the mixture is stirred for 3.5 hours under nitrogen (TLC, silica, hexane-ethyl acetate 65:35, UV). A small amount of insoluble material is filtered off and the filtrate is diluted with water. Removal of the ethanol in vacuo (bath temp. <30° C.) and trituration of the residue with water yields a brownish solid. The latter is collected, washed with water and dried in vacuo (over P₂O₅). The crude sodium salt (3.45 g) is slurried in ether-dichloromethane, filtered and washed with portions of cold ether and hexane. It is further purified by recrystallization from methanol (containing a small amount of dichloromethane and ethyl acetate)- ether (light yellow solid, 2.7 g, 72.5%). The corresponding acid is obtained by neutralizing a suspension of the sodium salt with 10% HOAc (to pH 6.5). The acid is extracted with ethyl acetate and the extracts are washed with water, dried (MgSO₄) and concentrated to small volume. The residue is diluted with hexane, the solid is collected, washed and dried in vacuo (off-white solid, m.p. darkens at 175° C., melts with dec. at 199°-201° C.).

IR (KBr, cm⁻¹): 1720 (CO)

NMR (DMSO-d₆, 400 MHz): δ3.69 (s, 2H, CH₂COO), 5.27 (s, 2H, OCH₂Ar), 6.31 (d, J=8.7 Hz, 1H, ArH), 6.80 (dd, 1H, ArH), 6.89 (s, 1H, NH), 7.02 (d, J=2.9 Hz, 1H, ArH), 7.08 (t, J=8.05 Hz, 1H, ArH), 7.4 (s, 1H, ArH), 7.46 (s, 1H, ArH), 7.64 (dd, 1H, ArH), 7.70 (d, J=8.5 Hz, 1H, ArH), 8.04 (m, 2H, ArH), 8.45 (d, J=8.5 Hz, 1H, ArH), 12.67 (s, 1H, COOH).

MS (CI, m/z): 493/491/489/487 (3 Cl, M+H)⁺, 469 (M-H₂O)⁺, 312, 178, 89 (b.p.).

Analysis for: $C_{24}H_{17}Cl_3N_2O_3$ (0.08% water). Calculated: C, 59.05; H, 3.51; N, 5.73. Found: C, 58.69; H, 3.55; N, 5.56.

EXAMPLE 7

2-[(2,6-Dichlorophenyl)amino]-5-[(2-naphthalenyl)methoxy]benzene acetic acid methyl ester A mixture of the compound of Example 1F (1.05 g, 3.25 mmol) finely powdered anhydrous potassium carbonate (0.450 g, 3.25 mmol), 18-crown-6 (0.050 g) and 2-bromomethylnaphthalene (0.75 g, 3.35 mmol) in dry acetonitrile (50 mL) is heated under nitrogen at 65° C. overnight. The solvent is evaporated and the residue partitioned between ethyl acetate and water (50 mL each). The organic phase is washed with brine and dried (MgSO₄). Removal of the solvent affords the crude product (1.6 g, brown oil). Trituration with methanol gives the pure product (white solid, 1.24 g, m.p. 92°-93° C., dec.).

IR (KBr, cm⁻¹): 3378 (NH), 1767 (CO)

NMR (CDCl₃, 400 MHz): δ3.74 (s, 3H, COOCH₃), 3.81 (s, 2H, CCH₂COO), 5.17 (s, 2H, OCH₂Ar), 6.55 (d, 1H, J=8.7 Hz, ArH), 6.61 (s, 1H, NH), 6.81 (dd, 1H, ArH), 6.90-6.95 (m, 2H, ArH), 7.30 (s, 1H, ArH), 7.32 (s, 1H, ArH), 7.47-7.54 (m, 3H, ArH), 7.82-7.87 (m, 4H, ArH).

MS (EI, m/z): 469/467/465 (2Cl, M)⁺, 328/326/324 (2Cl, b.p., M-C₁₁H₉)⁺.

Analysis for: $C_{26}H_{21}Cl_2NO_3$. Calculated: C, 66.96; H, 4.54; N, 3.00. Found: C, 67.03; H, 4.47; N, 2.98.

EXAMPLE 8

2-[(2,6-Dichlorophenyl)amino]-5-[(naphthalenyl)methoxy]benzene acetic acid

Under nitrogen, a solution of the compound of Example 7 (3.5 g, 7.5 mmol) in tetrahydrofuran (38 mL) and 1N LiOH (10 mL) is stirred overnight at ambient temperature. The solvent is evaporated and the residue partitioned between 0.1N HCl and ethyl acetate. The organic phase is washed with brine and dried (MgSO₄). Removal of the solvent in vacuo affords the crude acid as an orange oil which is redissolved in ethanol (20 mL) and converted to the sodium salt with 1N NaOH (10 mL). Removal of most of the ethanol gives a precipitate which is collected and washed with water. The crude salt is further purified by flash chromatography (on silica Merck 60, dichloromethane-methanol gradient, 100:0 98:2) to give 1.95 g of the pure sodium salt. A slurry of the purified salt in ethanol is acidified with 10% HOAc and the resulting solid is collected, washed with water and methanol and dried. Yield of the title compound: 0.860 g (79%, white solid, m.p. sintering at 148° C., melting at 158° C.).

IR (KBr, cm⁻¹): 3340 (NH), 1690 and 1715 (CO).

NMR (DMSO-d₆, 400 MHz): δ3.68 (s, 2H, CCH₂COO), 5.17 (s, 2H, OCH₂Ar), 6.32 (d, 1H, J=8.7 Hz, ArH), 6.80 (dd, 1H, ArH), 6.99 (d, 1H, J=2.8 Hz, ArH), 7.03 (broad s, 1H, NH), 7.07 (t, 1H, J=8 Hz, ArH), 7.45-7.57 (m, 5H, ArH), 7.89-7.96 (m, 4H, ArH).

MS (CI, m/z): 456/454/452 (2 Cl, b.p., M+H)⁺, 312 (M+H-141)⁺, 141 (C₁₁H₉)⁺.

Analysis for: $C_{25}H_{19}Cl_2NO_3$. Calculated: C, 66.38; H, 4.23; N, 3.09. Found: C, 67.50; H, 4.27; N, 3.02.

HPLC (C₁₈ Novapak, CH₃CN-ammonium phosphate buffer pH 3.5): purity 98.1%.

EXAMPLE 9

2-[(2,6-Dichlorophenyl)amino]-5-[(4-phenoxy)butoxy]benzene acetic acid

A. 2-[(2,6-Dichlorophenyl)amino]-5-[(4-phenoxy)butoxy]benzene acetic acid methyl ester A mixture of the compound of Example 1F (2.1 g, 6.4 mmol), finely powdered anhydrous potassium carbonate (0.89 g, 6.4 mmol), 18-crown-6 (0.100 g) and 4-phenoxybutylbromide (1.53 g, 6.7 mmol) in dry acetonitrile (100 mL) is heated at 65° C. under nitrogen for 24 hours. The solvent is removed and the residue partitioned between ethyl acetate and water (50 mL each). The organic phase is washed with brine, charcoalized, filtered (SolkaFloc) and dried (MgSO₄). Removal of the solvent affords the title product as a brown oil (2.8 g, used without further purification).

NMR (CDCl₃, 200 MHz): δ1.96 (m, 4H, CCH₂C), 3.74 (s, 3H, OCH₃), 3.82 (s, 2H, CCH₂COO), 4.02 (m, 4H, OCH₂C), 6.52 (d, 1H, ArH), 6.60 (s, 1H, NH), 6.70 (d, 1H, ArH), 6.80 (d, 1H, ArH), 6.85-7.0 (m, 4H, ArH), 7.25-7.35 (m, 4H, ArH).

B. 2-[(2,6-Dichlorophenyl)amino]-5-[(4-phenoxy)butoxy]benzene acetic acid

A solution of the ester of Step A, above (2.0 g, 4.2 mmol) in tetrahydrofuran (100 mL) and 1N LiOH (12.7 mL) is stirred under nitrogen overnight. The solvent is removed and the residue slurried in water. The mixture is acidified using dilute HCl and extracted with ethyl acetate (2×500 mL). The combined organic phases are washed with brine and dried (MgSO₄). Removal of the solvent affords a brown oil which crystallizes from acetonitrile (white solid, 0.620 g, approximately 90% pure by HPLC). This material is further purified by HPLC (Dynamax C18, 2"-column, acetonitrile-ammonium acetate buffer 3:2) to provide pure title compound (0.250 g, white solid, m.p. 128°-131° C., dec.).

IR (KBr, cm⁻¹): 3310 (NH), 1680 (CO).

NMR (CDCl₃, 400 MHz): δ1.95 (m, 4H, CCH₂C), 3.83 (s, 2H, CH₂COO), 4.02 (m, 4H, OCH₂C), 6.43 (s, 1H, NH), 6.55 (d, 1H, J=8.6 Hz, ArH), 6.70 (dd, 1H, ArH), 6.81 (d, 1H, J=2.8 Hz, ArH), 6.88-6.95 (m, 4H, ArH), 7.25-7.31 (m, 4H, ArH).

MS (EI, m/z): 463/461/459 (2 Cl, M)⁺, 149 [b.p., PhO(CH₂)₄]⁺.

Analysis for: $C_{24}H_{23}Cl_2NO_4$. Calculated: C, 62.62; H, 5.04; N, 3.04. Found: C, 62.85; H, 4.96; N, 3.00.

EXAMPLE 10

2-[(2,6-Dichlorophenyl)amino]-5-[(1-methyl-1H-benzimidazol-2-yl)methoxy]benzene acetic acid methyl ester To a solution of the compound of Example 1F (0.5 g, 1.53 mmol) in dimethylformamide (8 mL) is added potassium carbonate (0.17 g, 1.23 mmol), tetrabutylammonium iodide (0.347 g) and 2-bromomethyl-N-methyl benzimidazole (0.457 g, 2.53 mmol). The mixture is heated at 60° C. under nitrogen for 3 days. Upon addition of water to the cooled reaction mixture a greenish-brown precipitate is obtained which is extracted with ethyl acetate (3 times) and dried ($MgSO_4$). Removal of the solvent gives the crude product as a dark brown oil. This is purified by flash-chromatography (on silica Merck 60, preabsorbed in methylene chloride, eluted with toluene-ethyl acetate 85:15). The tan solid thus obtained is triturated twice with methanol and the resulting white solid is filtered, and dried (0.360 g, 50%, m.p. 162°-163° C. dec.).

IR (KBr, $cm^{-1}$): 1750, 1730 (CO)

NMR ($CDCl_3$, 400 MHz): δ3.73 (s, 3H, $COOCH_3$), 3.79 (s, 2H, $ArCH_2COO$), 3.88 (s, 3H, $NCH_3$), 5.32 (s, 2H, $ArCH_2O$), 6.52 (d, 1H, J=8.71 Hz, ArH), 6.63 (s, 1H, NH), 6.87 (dd, 1H, ArH), 6.91-6.98 (mm, 2H, ArH), 7.26-7.37 (mm, 5H, ArH), 7.77 (d, 1H, J=7.21 Hz, ArH).

MS (CI, m/z): 474/472/470 (b.p., 2 Cl, $M+H)^+$.

Analysis for: $C_{24}H_{21}Cl_2N_3O_3$. Calculated: C, 61.29; H, 4.50; N, 8.93. Found: C, 60.98; H, 4.24; N, 8.71.

EXAMPLE 11

2-[(2,6-Dichlorophenyl)amino]-5-[(1-methyl-1H-benzimidazol-2-yl)methyl]benzene acetic acid To a solution of the compound of Example 10 (1.5 g, 3.19 mmol) in ethanol (60 mL) is added 1N NaOH (13 mL) and the mixture is stirred for 3.5 hours under nitrogen. The ethanol is removed in vacuo (bath temp. 30° C.) and the residue triturated in water overnight to give a green solid. The crude sodium salt (1.15 g) is filtered, washed with water and dried (in vacuo). It is then suspended in water (low solubility) and neutralized with 10% HOAc (to pH=6.5) to yield the corresponding acid. The mixture is shaken with ethyl acetate and the insoluble product is filtered (0.374 g, title compound). The organic phase is evaporated (rotovap) to give additional product (0.3 g). The combined solids are triturated with ethyl ether (2 times), collected, washed with hexane and dried in vacuo overnight. The pure title compound is obtained as a tan solid (0.586 g, 40.0%, m.p. 183°-185° C. dec.).

IR (KBr, $cm^{-1}$): 1690 (CO)

NMR (DMSO, 400 MHz): δ3.69 (s, 2H, $ArCH_2COO$), 3.84 (s, 3H, $NCH_3$), 5.31 (s, 2H, $ArCH_2O$), 6.32 (d, 1H, J=8.73 Hz, ArH), 6.88 (dd, 1H, ArH), 6.93 (s, 1H, NH), 7.04 (d, 1H, J=2.92 Hz, ArH), 7.10 (t, 1H, J=16.12 Hz, ArH), 7.21 (t, 1H, J=16.91 Hz, ArH), 7.28 (t, 1H, J=16.26 Hz, ArH), 7.47 (m, 2H, ArH), 7.57 (d, 1H, J=8.03 Hz, ArH), 7.63 (d, 1H, J=7.88 Hz, ArH), 12.72 (broad s, 1H, OH).

MS (FAB, m/z): 460/458/456 (2 Cl, $M+H)^+$, 422 $(M+H-Cl)^+$, 91, 79 (b.p.)

Analysis for: $C_{23}H_{19}Cl_2N_3O_3$. Calculated: C, 60.54; H, 4.20; N, 9.21. Found: C, 60.25; H, 4.02; N, 9.21.

EXAMPLE 12

2-[(2,6-Dichlorophenylamino]-N-methoxy-[(2-quinolyl)methoxy]benzene acetamide

Under nitrogen, the compound of Example 2 (1 g, 2.2 mmol) is added portionwise to a stirred solution of triethylamine (0.75 mL, 5.4 mmol), 4-dimethylaminopyridine (0.12 g, 0.9 mmol), methoxyamine hydrochloride (0.225 g, 2.7 mmol) and 1-(3-dimethylaminopropyl)-3-ethylcarbodiimide hydrochloride (0.575 g, 3 mmol) in dichloromethane (50 mL). After overnight stirring at room temperature, the reaction mixture is diluted with 25 mL of dichloromethane and washed with water (50 mL) and brine. After drying ($MgSO_4$), the solvent is removed and the residual solid (1.1 g) purified by flash chromatography (on silica Merck 60, dichloromethane-ethyl acetate 19:1 9:1 for the removal of impurities; dichloromethane-methanol 98:2 for product recovery) to give the desired product (oil, 0.400 g). A white solid is obtained by crystallization of the oil from ethyl acetate-hexane (0.320 g, 30%, m.p. sinters at 155° C., melts at 160° C.).

IR (KBr, $cm^{-1}$): 3320 (NH), 1650 (CO).

NMR (DMSO-$d_6$, 400 MHz): δ3.42 (s, 2H, $CCH_2CO$), 3.56 (s, 3H, $NOCH_3$), 5.28 (s, 2H, $OCH_2Ar$), 6.30 (d, 1H, J=8.75 Hz, ArH), 6.80 (dd, 1H, ArH), 6.94 (d, 1H, J=2.8 Hz, ArH), 7.08 (t, 1H, J=8 Hz, ArH), 7.46 (d, 2H, J=8 Hz, ArH), 7.58-7.66 (m, 2H, ArH), 7.73-7.79 (m, 2H, ArNH+ArH), 7.99 (m, 2H, ArH), 8.4 (d, 1H, J=8.5 Hz, ArH), 11.46 (s, 1H, NHOC).

MS (FAB, m/z): 486/484/482 (2 Cl, $M+H)^+$, 292, 143, 79 (b.p.)

Analysis for: $C_{25}H_{21}Cl_2N_3O_3$. Calculated: C, 62.25; H, 4.39; N, 8.71. Found: C, 62.42; H, 4.24; N, 8.72.

EXAMPLE 13

1-(2,6-Dichlorophenyl-5-(2-quinolinylmethoxy)-2-indolinone

Under an atmosphere of nitrogen, a mixture of the compound of Example 1 F (3.48 g, 10.7 mmol), potassium carbonate (1.48 g, 10.7 mmol), 18-crown-6 (40 mg) and 2-chloromethylquinoline (1.92 g, 10.8 mmol) in 75 mL of acetonitrile is heated at reflux (80° C.) overnight. An additional 0.5 g of 2-chloromethylquinoline is added and the reaction mixture is heated at reflux for 24 hours. The solvent is removed by evaporation and the residue is partitioned between ethyl acetate and water. The organic phase is washed with brine and dried ($MgSO_4$). Removal of solvent affords 5.0 g of a brown oil. The crude product is purified by flash chromatography (silica Merck 60, hexane-ethyl acetate 1:1) to give 1.4 g (35%) of the product as an amber oil. It crystallizes from methanol ($CH_2Cl_2$) to give pure title product (0.933 g, buff colored needles, m.p. 147°-147.5° C.).

IR (KBr, $cm^{-1}$): 1730 (C=O).

NMR ($CDCl_3$, 400 MHz): δ3.72 (s, 2H, $CCH_2CON$), 5.33 (s, 2H, $OCH_2Ar$), 6.28 (d, 1H, J=8.4 Hz, ArH), 6.84 (dd, 1H, ArH), 7.05 (d, 1H, J=1.5 Hz, ArH), 7.33 (t, 1H, ArH), 7.45 (2s, 2H, ArH), 7.53 (t, 1H, ArH), 7.55 (d, 1H, ArH), 7.67 (t, 1H, ArH), 7.81 (d, 1H, J=8.4 Hz, ArH), 8.05 (d, 1H, J=8.2 Hz, ArH), 8.18 (d, 1H, J=8.4 Hz, ArH).

MS (EI, m/z): 434 $(M)^+$, 292, 258, 143 (b.p.).

Analysis for: $C_{24}H_{16}Cl_2N_2O_2$. Calculated: C, 66.22; H, 3.70; N, 6.43. Found: C, 65.83; H, 3.73; N, 6.32.

EXAMPLE 14

1-[2,6-Dichloro-4-(2-quinolinylmethoxy)phenyl]-1,3-dihydro-2H-indol-2-one

A. 2,6-Dichloro-4-methoxyaniline

A solution of 4-nitrosophenol [(6.85 g, 56 mmol, purified as described by Hays et al. J.O.C., 32, 153 (1967)] in toluene (200 mL) is saturated with HCl gas at 10° C. To the mixture is then added methanol (2 mL) and stirring is continued overnight at room temperature. The precipitate is filtered and the crude material (10.5 g) is purified by flash chromatography (on silica Merck-60, hexane-ethyl acetate 9:1) to provide the pure title compound (white solid, 2.6 g, 24%, m.p. 71°–73° C.: lit: m.p. 72°–73° C. from hot ethanol).

NMR (CDCl$_3$, 200 MHz): δ3.72 (s, 3H, OCH$_3$), 4.1 (broad, 2H, NH$_2$), 6.82 (s, 2H, ArH).

B. 2,6-Dichloro-4-methoxyacetanilide

To a mechanically stirred solution of the foregoing intermediate (4.94 g, 25.9 mmol) in glacial acetic acid (2.5 mL) is added dropwise acetyl chloride (1.92 mL, 27 mmol). The reaction mixture is then heated at 90° C. for 20 min. The solution is poured into ice-water (50 mL), the precipitate is collected, washed with water and dried. The crude product (white solid, 5.56 g, 92%, m.p. 184°–185° C.) is used in the next step without further purification.

NMR (CDCl$_3$, 200 MHz): δ2.22 (s, 3H, CH$_3$CO), 3.80 (s, 3H, OCH$_3$), 6.90 (s, 2H, ArH).

C. N-Phenyl-(2,6-dichloro-4-methoxy)-aniline

Under a nitrogen atmosphere, a mixture of 2,6-dichloro-4-methoxy acetanilide (5.5 g, 23.6 mmol), anhydrous powdered potassium carbonate (1.63 g, 11.8 mmol) and copper powder (0.16 g) in bromobenzene (55 mL) is heated at reflux for 3 hrs. The excess bromobenzene is then removed by steam distillation. In place of the steam distillation, the excess bromobenzene can be removed by azeotropic distillation following addition of water to the crude product mixture. This procedure is repeated until no bromobenzene can be detected in the azeotrope. The residue is partitioned between water and ether (30 mL each), the organic phase is washed with brine (30 mL) and dried (MgSO$_4$). Removal of the solvent affords the intermediate N-phenyl-2,6-dichloro-4-methoxy acetanilide (6.7 g). The latter is refluxed for 6 hrs. in 10% ethanolic KOH (50 mL) under nitrogen. The solvent is evaporated and the residue diluted with water (50 mL). The precipitate is collected, washed with water and dried in vacuo (over P$_2$O$_5$) to give the title product (5.4 g, 86%, light brown solid).

NMR (CDCl$_3$, 400 MHz): δ3.81 (s, 3H, OCH$_3$), 5.47 (s, 1H, NH), 6.62 (d, 2H), J=7.6 Hz, ArH), 6.85 (m, 1H, ArH), 6.96 (s, 2H, ArH), 7.20 (t, 2H, J=7.6 Hz, ArH)

MS (EI, m/z): 271/269/267 (2 Cl, b.p., M)$^+$, 252 (M-CH$_3$)$^+$

Analysis for: C$_{13}$H$_{11}$Cl$_2$NO. Calculated: C, 58.23; H, 4.13, N, 5.22. Found: C, 57.84; H, 4.09; N, 5.13.

D. N-[(2,6-Dichloro-4-methoxy)phenyl]-N-phenyl chloroacetamide

Under anhydrous conditions, a mixture of N-phenyl-(2,6-dichloro-4-methoxy)aniline (5.3 g, 19.9 mmol) and chloroacetyl chloride (26 mL) is heated at reflux for 1 hr. The excess of the acid chloride is evaporated in vacuo and the residue is partitioned between saturated NaHCO$_3$ and ethyl acetate (30 mL each). The organic phase is washed with brine (30 mL) and dried (Na$_2$SO$_4$). Removal of the solvent affords the title compound as a 1:1 mixture of rotamers (6.7 g, light brown solid). It is used in the next step without further purification.

NMR (DMSO-d$_6$, 400 MHz): δ3.81 and 3.84 (2s, 3H, OCH$_3$), 4.09 (s, 1H, COCH$_2$Cl), 4.43 (s, 1H, COCH$_2$Cl), 7.21–7.50 (m, 7H, ArH)

MS (EI, m/z): 349/347/345/343 (3 Cl, M)$^+$, 152 (b.p.), 77

E. 1-[(2,6-Dichloro-4-hydroxy)phenyl]-1,3-dihydro-2H-indol-2-one

A homogeneous mixture of N-[(2,6-dichloro-4-methoxy)phenyl]-N-phenyl chloroacetamide (0.5 g, 1.45 mmol) and aluminum chloride (0.5 g) is heated under nitrogen at 250° C. with mechanical stirring for 15 min. It is then allowed to cool to 160° C. and kept at this temperature for another hour. The brown solid mass is treated with water (50 mL) and extracted with ethyl acetate (2×50 mL). The organic phase is washed with brine and dried (MgSO$_4$). Removal of the solvent yields a brown foam which is triturated with ether to provide the title compound as a light brown solid (0.37 g, 87%, m.p. sintering at 195° C., melting at 200° C.) which can be recrystallized from methanolisopropanol without change in the m.p.

NMR (DMSO-d$_6$, 200 MHz): δ3.80 (s, 2H, CH$_2$CO), 6.40 (d, 1H, ArH), 7.06 (m, 3H, ArH), 7.18 (t, 1H, ArH), 7.32 (d, 1H, ArH), 10.80 (broad, 1H, ArH).

MS (EI, m/z): 297/295/293 (2 Cl, M)$^+$, 230 (b.p., 258-CO)$^+$.

F. 1-[2,6-Dichloro-4-(2-quinolinylmethoxy)phenyl]-1,3-dihydro-2H-indol-2-one

A mixture of the indolinone (1.6 g, 5.46 mmol), of step E, powdered anhydrous K$_2$CO$_3$ (1.12, 8.1 mmol), 18-crown-6 (50 mg) and dry acetonitrile (50 mL) is stirred at ambient temperature for 30 min. 2-Chloromethylquinoline hydrochloride (1.17 g, 5.46 mmol) is then added and the mixture is heated for 4 hours at 90° C. The solvent is removed and the residual solid washed with water and dried in vacuo. It is recrystallized from dichloromethane-methanol to provide the pure title compound (light grey solid, 1.55 g, 64%, m.p. sintering at 152° C., melting at 158° C.).

IR (KBr, cm$^{-1}$): 1740 (CO)

NMR (CDCl$_3$, 400 MHz): δ3.74 (s, 2H, CCH$_2$CO), 5.41 (s, 2H, ArCH$_2$O), 6.41 (d, 1H, J=7.8 Hz, ArH), 7.08 (t, 1H, J=7.5 Hz, ArH), 7.21 (m, 3H, ArH), 7.31 (d, 1H, J=7.1 Hz, ArH), 7.58 (t, 1H, J=8 Hz, ArH), 7.63 (d, 1H, J=8.4 Hz, ArH), 7.77 (dt, 1H, ArH), 7.86 (d, 1H, J=7.6 Hz, ArH), 8.1 (d, 1H, J=8.5 Hz, ArH), 8.25 (d, 1H, J=8.5 Hz, ArH).

MS (+FAB, m/z): 435 (M+H)$^+$ 294, 143.

Analysis for: C$_{24}$H$_{16}$Cl$_2$N$_2$O$_2$. Calculated: C, 66.22; H, 3.70; N, 6.43. Found: C, 65.86; N, 3.68; N, 6.37.

EXAMPLE 15

1-Phenyl-5-(2-quinolinylmethoxy)-1,3-dihydro-2H-indol-2-one

A. (2-Phenylamino-5-hydroxy)-benzene acetic acid methylester

A mixture of 2-[(2,6-dichlorophenyl)amino]-5-hydroxy benzene acetic acid methylester (3.25 g, 10 mmol) of Example 2F, triethylamine (3.06 mL, 22 mmol) and 5% palladium on carbon (50 mg) in methanol (10 mL) is hydrogenated at room temperature and atmospheric pressure. After an uptake of 430 mL of hydrogen, the reaction is filtered (Solka Floc) and the solvent evaporated to yield a light yellow solid (2.5 g, 97% pure by NMR). An analytical sample is prepared by trituration of the crude product with hexane-ethyl acetate. The pure material melts at 102°-103° C. and it is sensitive to air, light and heat.

NMR (CDCl₃, 400 MHz): δ3.60 (s, 2H, CCH₂CO), 3.68 (s, 3H, OCH₃), 4.67 (s, 1H, NH), 6.02 (s, 1H, OH), 6.72-6.80 (m, 5H, ArH), 7.16-7.23 (m, 3H, ArH)

MS (EI, m/z): 257 (M)⁺, 266 (M-OCH₃)⁺, 196 (b.p.)

Analysis for: C₁₅H₁₅NO₃. Calculated: C, 70.02; H, 5.88; N, 5.44. Found: C, 70.01; H, 5.74; N, 5.35.

B. 2-(Phenylamino)-5-(2-quinolinylmethoxy)benzene acetic acid methyl ester

A mixture of the phenol (1.78 g, 6.9 mmol) of step A, powdered anhydrous potassium carbonate (1.03 g, 7.4 mmol), tetrabutylammonium iodide (0.350 g) and dry acetonitrile (50 mL) is stirred at room temperature under nitrogen for 15 min. To the slurry is added 2-chloromethylquinoline (1.6 g, 7.5 mmol) and the mixture is heated at 65° C. for 72 hrs. The solvent is removed and the residue is partitioned between water and ethyl acetate (50 mL each). The organic phase is washed with brine and dried (MgSO₄). The solvent is evaporated and the residue (3.9 g, thick brown oil) is flash chromatographed (on silica Merck 60, eluant hexane-ethyl acetate 9:1 and 3:1) to yield the title compound (white solid, 1.02 g, 37%, m.p. 106°-107° C.).

NMR (DMSO-d₆, 400 MHz): δ3.43 (s, 3H, COOCH₃), 3.61 (s, 2H, CCH₂COO), 5.33 (s, 2H, OCH₂Ar), 6.58-6.63 (m, 3H, ArH), 6.96 (m, 1H, ArH), 7.04-7.10 (m, 4H, ArH), 7.21 (s, 1H, NH), 7.61 (s, 1H, NH), 7.61 (t, 1H, J=7 Hz, ArH), 7.69 (d, 1H, J=8.49 Hz, ArH), 7.78 (t, 1H, J=7 Hz, ArH), 8.0 (t, 2H, J=8.5 Hz, ArH), 8.42 (d, 1H, J=8.5 Hz, ArH).

MS (EI, m/z): 398 (M)⁺ 256, 224 (b.p. 256-CH₃OH)⁺

Analysis for: C₂₅H₂₂N₂O₃. Calculated: C, 75.36; H, 5.56; N, 7.03. Found: C, 75.23; H, 5.31; N, 6.96.

C. 1-Phenyl-5-(2-quinolinylmethoxy)-1,3-dihydro-2H-indol-2-one

A solution of the ester (1.2 g, 2.46 mmol) of Step B in methanol (20 mL) containing 1N NaOH (10 mL) is stirred at room temperature under nitrogen overnight. The solid is collected, washed with water and dried in high vacuum to give the product (0.81 g, m.p. 148°-149° C., white solid). Recrystallization of the crude product from ethyl acetate provides pure title compound (0.32 g, 35.5%, m.p. 148°-149° C.).

NMR (DMSO-d₆, 400 MHz): δ3.71 (s, 2H, CCH₂CO), 5.33 (s, 2H, OCH₂Ar), 6.62 (d, 1H, J=8.5 Hz, ArH), 6.90 (dd, 1H, ArH), 7.13 (d, 1H, J=2.3 Hz, ArH), 7.37-7.42 (m, 3H, ArH), 7.51-7.54 (m, 2H, ArH), 7.60 (t, 1H, J=7 Hz, ArH), 7.66 (d, 1H, J=8.5 Hz, ArH), 7.77 (dt, 1H, ArH), 7.99 (t, 2H, J=8.4 Hz, ArH), 8.40 (d, 1H, J=8.5 Hz, ArH)

MS (EI, m/z): 366 (M)⁺, 224 (b.p.), 167

Analysis for: C₂₄H₁₈N₂O₂. Calculated: C, 78.67; H, 4.95; N, 7.65. Found: C, 78.62; H, 4.93; N, 7.77.

EXAMPLE 16

2-(Phenylamino)-5-(2-quinolinylmethoxy)benzene acetic acid

A solution of the ester (1 g, 2.5 mmol) of Example 15B in methanol (30 mL) containing 1N NaOH (20 mL) is heated at reflux for 3 hours under nitrogen. The solid obtained upon cooling is collected, washed with water and dried in vacuo. The sodium salt thus obtained (yellow solid, 0.94 g) is dissolved in a mixture of methanol and water (4:1) and neutralized with glacial acetic acid (0.13 mL, 2.3 mmol). The product is collected and dried (0.76 g, 79%, m.p. sintering at 105° C., melting at 126°-128° C.).

NMR (DMSO-d₆, 400 MHz): δ3.53 (s, 2H, CCH₂CO), 5.32 (s, 2H, OCH₂Ar), 6.62 (m, 3H, ArH), 6.95 (dd, 1H, ArH), 7.04-7.12 (m, 4H, ArH), 7.22 (s, 1H, NH), 7.61 (t, 1H, J=7.1 Hz, ArH), 7.69 (d, 1H, J=8.5 Hz, ArH), 7.78 (dt, 1H, ArH), 8.0 (t, 2H, J=9.1 Hz, ArH), 8.42 (d, 1H, J=8.5 Hz, ArH), 12.21 (s, 1H, COOH)

MS (+FAB, m/z): 385 (M+H)⁺, 91 (b.p.)

Analysis for: C₂₄H₂₀N₂O₃. Calculated: C, 74.98; H, 5.24; N, 7.29. Found: C, 75.05; H, 5.30; N, 7.33.

EXAMPLE 17

2-[(2,6-Dichlorophenyl)amino]-5-(3-phenoxybenzyl)-benzene acetic acid

A. 2-[(2,6-Dichlorophenyl)amino]-5-(3-phenoxybenzyl)benzene acetic acid methyl ester A mixture of 2-[(2,6-dichlorophenyl)amino]-5-hydroxy benzene acetic acid methyl ester (2.5 g, 7.67 mmol) of Example 2F, powdered anhydrous potassium carbonate (0.55 g, 4 mmol), tetrabutylammonium iodide (0.050 g) and dry acetonitrile (50 mL) is stirred at room temperature under nitrogen for 30 min. To the slurry is then added 3-phenoxybenzylchloride (2 g, 9.17 mmol) and the mixture is placed in an oil bath maintained at 65°-70° C. overnight. The solvent is removed and the residue partitioned between water and ethyl acetate (50 mL each). The organic phase is washed with brine and dried (Na₂SO₄). The solvent is evaporated and the residue (brown oil, 4.2 g) is purified by flash chromatography (on silica Merck 60, hexane-ethyl acetate 85:15) to give the title product (yellow oil, 2.83 g, 73%).

NMR (DMSO-d₆, 200 MHz): δ3.63 (s, 3H, OCH₃), 3.78 (s, 2H, CCH₂CO), 5.0 (s, 2H, OCH₂Ar), 6.30 (m, 1H, ArH), 6.75 (m, 2H, NH+ArH), 6.90-7.25 (m, 8H, ArH), 7.30-7.50 (m, 5H, ArH)

B. 2-[(2,6-Dichlorophenyl)amino]-5-(3-phenoxybenzyl)-benzene acetic acid salt with 2-amino-2-(hydroxymethyl)-1,3-propanediol A solution of the ester (2.2 g, 4.3 mmol) of Step A in dioxane (20 mL) containing 1N NaOH (7 mL) is heated at reflux under nitrogen for 4 hrs. The solvent is removed and the residue is partitioned between dilute HCl and ether (30 mL each). The organic phase is washed with brine, dried (Na₂SO₄) and filtered. The filtrate is treated with tris(hydroxymethyl)aminomethane (0.485 g) in methanol (20 mL). The solvent is evaporated to a syrup in vacuo and diluted with ethyl acetate. The crystalline solid is collected (white solid, 1.6 g, 60%) and recrystallized from methanol-water to provide the pure title compound (0.89 g, m.p. 137°-138° C.).

NMR (DMSO-d₆, 400 MHz): δ3.41 (s, 6H, OCH₂C), 3.43 (s, 2H, CCH₂CO), 4.99 (s, 2H, OCH₂Ar), 6.23 (d, 1H, J=8.7 Hz, ArH), 6.62 (dd, 1H, ArH), 6.79 (d, 1H, J=2.9 Hz, ArH), 6.93 (dd, 1H, ArH), 6.99-7.06 (m, 3H, ArH), 7.06 (t, 1H, ArH), 7.13 (dt, 1H, ArH), 7.19 (d, 1H, J=7.5 Hz, ArH), 7.36-7.42 (m, 5H, ArH), 8.81 (broad, exchanged with D₂O, 1H, NH).

MS (+FAB/mz/): 493 (M)⁺

Analysis for: C₃₁H₃₂Cl₂N₂O₇. Calculated: C, 60.49; H, 5.24; N, 4.55. Found: C, 60.33; H, 5.24; N, 4.63.

C.
2-[(2,6-Dichlorophenyl)amino]-5-(3-phenoxybenzyl)-benzene acetic acid

A suspension of the salt (0.575 g, 0.93 mmol) of Step B in a mixture of ether and water (5 mL each) is acidified with 1N HCl (to pH 5.5). The layers are separated and the organic phase is washed with brine. After drying ($Na_2SO_4$) the filtrate is concentrated to ca. 2 mL. Crystallization is induced by the addition of hexane. The crystals are collected and dried to provide the pure title compound (white solid, 0.33 g, m.p. 116°–117° C. with yellowing at 112° C.).

NMR (DMSO-$d_6$m, 400 MHz): δ3.67 (s, 2hH, $CCH_2CO$), 5.01 (s, 2H, $OCH_2Ar$), 6.31 (d, 1H, ArH), 6.73 (dd, 1H, ArH), 6.88 (s, 1H, NH), 6.91–7.2 (m, 8H, ArH), 7.35–7.40 (m, 3H, ArH), 7.46 (d, 1H, J=8 Hz, ArH), 12.69 (s, 1H, COOH)

MS (El, m/z): 497/495/493 (2 Cl, M)$^+$, 475 (M-$H_2O$)$^+$, 310, 292 (b.p., 310–$H_2O$)$^+$

Analysis for: $C_{27}H_{21}Cl_2NO_4$. Calculated: C, 65.60; H, 4.28; N, 2.83. Found: C, 65.46; H, 4.24; N, 2.83.

EXAMPLE 18

1-(2,6-Dichlorophenyl)-5-[7-chloro-2-(quinolinylmethoxy)]-1,3-dihydro-2H-indol-2-one The title compound is prepared utilizing the procedure of Example 15C but starting with 2-[(2,6-dichlorophenyl)amino]-5-(7-chloro-2-quinolinylmethoxy)-benzene acetic acid methyl ester of Example 5. The crude material is flash chromatographed (on silica Merck 60, preabsorbed in dichloromethane, eluted with hexane-ethyl acetate 8:2) to provide an off-white solid which is recrystallized from ethyl acetate. The crystals are washed with hexane and dried, m.p. 175°–176° C.

NMR ($CDCl_3$, 400 MHz): δ3.74 (s, 2H, $CH_2CO$), 5.32 (s, 2H, $ArCH_2O$), 6.29 (d, 1H, J=8.5 Hz, ArH), 6.84 (dd, 1H, J=8.5 Hz, ArH), 7.06 (s, 1H, ArH), 7.33–7.52 (m, 4H, ArH), 7.67 (d, 1H, J=8.5 Hz, ArH), 7.76 (d, 1H, J=8.7 Hz, ArH), 8.06 (s, 1H, ArH), 8.17 (d, 1H, J=8.5 Hz, ArH)

MS (E1, m/z): 474/472/470/468 (3 chlorines, M)$^+$, 205/203/201 (2 chlorines, M-267)$^+$, 294/292 (1 chlorine, b.p.)

Analysis for: $C_{24}H_{15}Cl_3N_2O_2$. Calculated: C, 61.36; H, 3.22; N, 5.96. Found: C, 61.16; H, 3.15; N, 5.88.

EXAMPLE 19

The compounds 5- and 12-hydroxyeicosatetraenoic acid (5-HETE and 12-HETE) and $LTB_4$ are early arachidonic acid oxidation products in the lipoxygenase cascade, which have been shown to mediate several aspects of inflammatory and allergic response. This is especially true with respect to 5,12-diHETE, which is also denoted as $LTB_4$ [see Ford-Hitchinson, *J. Roy. Soc. Med.*, 74, 831 (1981)]. Compounds which inhibit the $PLA_2$-mediated release of arachidonic acid thereby effectively prevent the oxidation of arachidonic acid to the various leukotriene products via the lipoxygenase cascade. Accordingly, the specificity of action of $PLA_2$ inhibitors can be determined by the activity of test compounds in this assay, which measures the ability of compounds to inhibit the synthesis of $LTB_4$ by rat glycogen-elicited polymorphonuclear leukocytes (PMN) in the presence of exogenous substrate.

The assay is carried out as follows:

Rat polymorphonuclear leukocytes (PMNs) are obtained from female Wistar rats (150-200 g) which receive an injection of 6% glycogen (10 ml i.p.). Rats are sacrificed 18-24 hours post injection by $CO_2$ asphyxiation and the elicited cells are harvested by peritoneal lavage using physiological saline (0.9% NaCl). The exudate is centrifuged at 400×g for 10 minutes. The supernatant fluid is discarded and the cell pellet is resuspended to a concentration of $2.0 \times 10^7$ cells/ml in HBSS containing $Ca^{++}$ and $Mg^{++}$ and 10 μM L-cysteine.

To 1 ml aliquots of cell suspension, test drugs or vehicle are added, then preincubated at 37° C. for 10 minutes. A 23187 (1 μM), [$^3$H]-AA (3.0 μCi/ml) and unlabeled AA (1 μM) are then added and the samples are further incubated for 10 minutes. The reaction is terminated by centrifugation and pelleting cells. Supernatants are then analyzed by HPLC analysis on a 15 cm×4.6 mm ID supelcosil LC-18 (Supelco)(3M) column, using a two solvent system at a flow rate of 1.4 ml total flow as follows:

Solvent A: 70:30 17.4 mM $H_3PO_4$:$CH_3CN$
Solvent B: $CH_3CN$
Gradient: (system is equillibrated with Solvent A)

| Time | Percent A | Percent B |
| --- | --- | --- |
| 0 | 100 | 0 |
| 15.0 | 100 | 0 |
| 20.0 | 65 | 35 |
| 40.0 | 65 | 35 |
| 42.0 | 10 | 90 |
| 50.0 | 10 | 90 |
| 50.1 | 100 | 0 |

Percent solvent changes are accomplished in a linear fashion.

Injections: 150 μl of each supernatant is injected directly onto column and $^3$H arachidonic acid metabolites are monitored using an on-line radioactivity detector (Ramona, IN/US, Fairfield, NJ).

Standards: $10^4$–$2.0 \times 10^4$ dpm of eicosanoids of interest are injected in 90 μl EtOH cocktail.

Co-chromatography with standard [$^3$H] leukotriene $B_4$ ($LTB_4$) in medium of stimulated PMN exposed to drug is compared to that found in medium of stimulated cells exposed to no drug, generating percent inhibition.

Results are expressed as percent inhibition at a given compound dose or as an $IC_{50}$ value.

Testing compounds of the invention in this assay give the following results:

TABLE I

| Compound of Example No. | % Inhibition | | $IC_{50}$ (μM) |
| --- | --- | --- | --- |
| diclofenac | NA | (stimulates) | |
| 1 | 96 | (at 0.5 μM) | |
| 2 | | | 0.01 |
| 3 | | | 0.02 |
| 4 | | | >0.01/<0.1 |
| 5 | 56 | (at 0.5 μM) | |
| | 95 | (at 10 μM) | |
| 6 | 80 | (at 0.5 μM) | |
| 7 | 34 | (at 10 μM) | |
| 8 | 67 | (at 0.5 μM) | |
| 9 | 16 | (at 0.5 μM) | |
| | 100 | (at 10 μM) | |
| 10 | 65 | (at 0.5 μM) | |
| 11 | −6* | (at 0.5 μM) | |
| 12 | 70 | (at 0.5 μM) | |
| 13 | 89 | (at 0.5 μM) | |
| 15 | 40 | (at 0.5 μM) | |

TABLE I-continued

| Compound of Example No. | % Inhibition | IC$_{50}$ ($\mu$M) |
|---|---|---|
| 16 | 90 (at 0.5 $\mu$M) | |

NA - Not Active
*a negative value denotes potentiation of cyclooxygenase (PGE$_2$ synthesis)

EXAMPLE 20

The procedure of Example 19 is also employed for the determination of the extent to which compounds of the invention inhibit the synthesis of the arachidonic acid cyclooxygenase oxidation product TxB$_2$.

In this assay, the procedure of Example 19 is carried out as described. However, in order to determine cyclooxygenase activity, the samples are co-chromatographed with authentic reference [$^3$H]-TxB$_2$.

The results are calculated as in Example 19 and presented below:

TABLE II

| Compound of Example No. | % Inhibition | IC$_{50}$ ($\mu$M) |
|---|---|---|
| diclofenac | | 0.03 |
| 1 | 4 (at 0.5 $\mu$M) | |
| 2 | | ca 10 |
| 3 | | >1 |
| 4 | | 3.7 |
| 5 | 0 (at 0.5 $\mu$M) | |
|   | 27 (at 10 $\mu$M) | |
| 6 | 26 (at 0.5 $\mu$M) | |
| 7 | −26* (at 0.5 $\mu$M) | |
| 8 | 30 (at 0.5 $\mu$M) | |
| 9 | 38 (at 0.5 $\mu$M) | |
|   | 100 (at 10 $\mu$M) | |
| 10 | 32 (at 0.5 $\mu$M) | |
| 11 | −8* (at 0.5 $\mu$M) | |
| 12 | −2* (at 0.5 $\mu$M) | |
| 13 | 10 (at 0.5 $\mu$M) | |
| 15 | −9* (at 0.5 $\mu$M) | |
| 16 | 10 (at 0.5 $\mu$M) | |

*Negative values denote a potentiation of cyclooxygenase (PGE$_2$ synthesis)

EXAMPLE 21

The compounds of the invention are tested in an in vitro isolated phospholipase A$_2$ assay to determine the ability of the test compounds to inhibit the release of arachidonic acid from an arachidonic acid-containing substrate by the action of phospholipase A$_2$ enzyme from human and non-human sources.

This assay is carried out as follows:

Into a 15 mL polypropylene tube are added the following:

| Agent | Volume, $\mu$L | Final Conc. |
|---|---|---|
| $^3$H-AA E. coli substrate[1] | 25 | 5 nmoles PL |
| CaCl$_2$ (0.1M)[2] | 5 | 5 mM |
| Tris-HCl (0.5M) pH 7.5[3] | 20 | 100 mM |
| Water[4] | 25 | |
| Drug/vehicle[5] | 1 | 50 $\mu$M* |
| PLA$_2$[6] | 25 | Volume yielding 12% hydrolysis in 10 min. |
| | 100 | |

*pre-incubate at room temperature 30 min prior to substrate addition.
[1]Prepared by adding 2 mL deionized and distilled water to 2 mL $^3$H-arachidonate labeled E. coli (lower count), to which is added 1 mL of $^3$H-arachidonate labeled E. coli (higher count) to yield a total of 5 m substrate (containing 1000 nmoles phospholipid).
[2]Stock 0.1 m CaCl$_2$, required for enzyme activity.
[3]Stock 0.5 m Trisma-Base
Stock 0.5M Trisma-HCl. Adjust pH to 7.5 (optimum for enzyme).
[4]Deionized and distilled water.
[5]Stock 10 mM prepared in dimethyl sulfoxide. Make 1:2 dilution with dimethyl sulfoxide and add 1 $\mu$L to 100 $\mu$L assay tube.
[6]Two human PLA$_2$ enzymes are used:
a) Semi-purified human platelet acid extract PLA$_2$ (in 10 mM sodium acetate buffer, pH 4.5). Remove protein precipitate by centrifugation at about 2200 rpm for 10 minutes.
b) Purified human synovial fluid.

Incubate the 100 $\mu$L reaction mixture for 10 minutes at 37° C. in a shaking water bath. The reaction is terminated by the addition of 2 mL tetrahydrofuran, followed by vortexing. NH$_2$ columns (100 $\mu$g/mL—Analytichem International) are conditioned with 0.5 mL tetrahydrofuran followed by 0.5 mL tetrahydrofuran/water (2 mL:0.1 mL, v/v).

The sample is loaded onto the columns and slowly drawn through them. The hydrolyzed arachidonic acid retained in the columns is eluted therefrom with 1 mL tetrahydrofuran/glacial acetic acid (2%). The arachidonic acid is transferred to scintillation vials and quantitated by $\beta$-counting analysis. A "total counts" sample is prepared by pipetting 25 $\mu$L $^3$H-arachidonate E. coli directly into a scintillation vial to which is added 1 mL tetrahydrofuran. 10 mL aquasol (scintillation cocktail) is added to all samples.

Calculations:

$$\% \text{ hydrolysis} = \frac{[^3\text{H}]\text{AA dpm(sample)} - [^3\text{H}]\text{AA dpm(nonspecific hydrolysis)}}{\text{total counts dpm}} \times 100$$

$$\% \text{ change} = \frac{\text{vehicle dpm} - \text{drug dpm}}{\text{vehicle dpm}} \times 100$$

Activity of Standard Drugs:

| Drug | IC$_{50}$ ($\mu$M) | |
|---|---|---|
| | Human Platelet PLA$_2$ | Human Synovial PLA$_2$ |
| Arachidonic Acid | 8.6 | 3.2 |
| Monoalide | 25.2 | 0.14 |

When tested in this assay, the compounds of the invention gave the following results:

TABLE III

| Compound of Example No. | % Inhibition at 10 $\mu$M | | IC$_{50}$ ($\mu$M) | |
|---|---|---|---|---|
| | HP* | HSF** | HP | HSF |
| diclofenac | 23 | 0 | | |
| 2 | | | — | 6.3 |
| 3 | | 21.7 | | |
| 5 | −5.3*** | −127*** | | |
| 6 | −8.6*** | 38.8 | | |
| 7 | 3.6 | −65.4*** | | |
| 8 | −3.9*** | 42.5 | | |
| 9 | 2.2 | 15.7 | | |
| 11 | — | 33.3 | | |
| 12 | — | −41.5*** | | |
| 13 | 12.5 (at 50 SM) | −11*** | | |
| 15 | — | −24*** | | |

TABLE III-continued

| Compound of Example No. | % Inhibition at 10 μM HP* | HSF** | IC$_{50}$ (μM) HP | HSF |
|---|---|---|---|---|
| 16 | 14.2 | −4.3*** | | |
| 18 | 2.2 | 5.1 | | |

*human platelet
**human synovial fluid
***negative values denote a potentiation of HP or HSF.

The compound of Example 2 is further tested in vitro in this assay against PLA$_2$ derived from a variety of sources. The results are summarized in Table IV.

TABLE IV

| % Inhibition at a concentration of 10 μM | | | | | |
|---|---|---|---|---|---|
| HP | HSF | Rabbit Chondrocyte | Rat Peritonitis Fluid | Pancreatic Lipase | Bee Venom |
| 12.7 | 47.6 | 84.± | 69.7 | 90.1 | 38.7 |

The results indicate that the compound tested is extremely effective in inhibiting the arachidonic acid releasing PLA$_2$ enzyme from a variety of sources.

EXAMPLE 22

The ability of the compounds of the invention to inhibit paw edema induced by the exogenous administration of PLA$_2$ is measured in the in vivo PLA$_2$ murine paw edema assay.

The assay is carried out as follows:

Non-fasted, male CD-1 mice (8 weeks old; 31-36 grams) are placed in plastic boxes in groups of six. The right hind paw volume is measured using mercury plethysmography (zero time). Compounds are dosed orally (0.5 ml of 0.5% Tween-80) 1 or 3 hours prior to PLA$_2$ injection or intravenously (0.2 ml in 0.3% dimethylsulfoxide/saline) 3 minutes prior to PLA$_2$ injection. A solution of purified PLA$_2$, from the diamond back cotton mouth snake (A. piscivorus piscivorus) is prepared in saline at a concentration of 6 μg/ml. Fifty (50) μl (0.3 μg) of this PLA$_2$ solution is injected subcutaneously into the right hind paw with a plastic 1 ml plastic syringe (27 gauge, 1″ needle). Paw volume of the injected paw is measured again at 10 minutes, 30 minutes and 60 minutes after PLA$_2$ injection. Animals are euthanized with CO$_2$ at the completion of the study.

The paw edema is calculated by subtracting the zero time volume from the volume recorded at each time period. Mean paw edema for each treatment group is then calculated and expressed as (μl±S.E.). Drug effects are expressed as a percent change from control (vehicle) values. Statistical significance is determined by a one-way analysis of variance with LSD comparison to control (p<0.05). ED$_{50}$'s are determined using repression analysis.

The activity of standard drugs in this assay is as follows:

| Compound | ED$_{50}$ mg/kg p.o. at +10 min |
|---|---|
| Cyproheptadine | 3.1 |
| BW755C | 50 |
| Dexamethasone* | 10 |
| Naproxen | 18 |
| Aristolochic Acid** | Not Active |
| Luffarrellolide** | Not Active |

*p.o. - 3 hr
**Some activity (30% inhibition) only when co-injected with enzyme.

When tested in this assay, the compounds of the invention gave the following results:

TABLE V

| Compound of Example No. | Dose mg/kg | % Change in Edema | | | |
|---|---|---|---|---|---|
| | | 3 min | 10 min | 30 min | 60 min |
| diclofenac | 10 (i.v.)* | — | −19 | −15 | −1 |
| | 100 (p.o.)** | — | −28 | −38 | −15 |
| 1 | 1 (i.p.)*** | −10 | −31 | −23 | — |
| | 10 (i.p.) | −39 | −77 | −37 | — |
| 2 | 10 (i.v.) | — | −45 | −37 | −32 |
| | 100 (p.o.) | — | −52 | −48 | −28 |
| 3 | 10 (i.p.) | — | +12 | −10 | +12 |
| 6 | 1 (i.p.) | −4 | −18 | −12 | — |
| | 10 (i.p.) | — | −24 | −24 | −32 |
| | 50 (.p.o) | — | −18 | −39 | −10 |
| 7 | 1 (i.p.) | — | −54 | −44 | — |
| | 10 (i.p.) | — | −32 | −39 | — |
| 8 | 10 (i.p.) | — | −28 | −43 | −47 |
| | 50 (p.o.) | — | +35 | −37 | −24 |
| 9 | 10 (i.p.) | −41 | −54 | −32 | — |
| | 50 (p.o.) | +37 | −12 | −4 | — |
| 10 | 1 (i.p.) | — | −29 | −20 | — |
| | 10 (i.p.) | — | −49 | −36 | — |
| 12 | 10 (i.p.) | — | −15 | −45 | −28 |
| | 50 (p.o.) | — | −2 | −36 | −22 |

*intravenous
**peroral
***intraperitoneal

The results show that the compounds of the invention are very effective in vivo in inhibiting edema induced by the exogenous administration of snake venom PLA$_2$.

EXAMPLE 23

The compounds of the invention are evaluated for their ability to inhibit the lipoxygenase and/or cyclooxygenase pathways of arachidonic acid metabolism in the in vivo murine zymosan peritonitis assay.

This assay is carried out as follows:

Male CD-1 mice (8 weeks old) are placed in plastic boxes in groups of six. Animals are injected with 1 ml i.p. of either 1% zymosan in pyrogen free 0.9% saline or saline (unstimulated control). Compounds are dosed orally 1 hour prior to zymosan injection. Twenty minutes after zymosan injection, the mice are asphyxiated by CO$_2$ inhalation and the peritoneal cavity is lavaged with 2 ml ice cold Hanks Balanced Salt Solution (HBSS) without CaCl$_2$, MgSO$_4$·7H$_2$O and MgCL$_2$·6H$_2$O. Peritoneal lavage fluid from each mouse is removed by syringe and placed in 5 ml plastic test tubes put on ice and volume is noted. Preparation of samples for evaluation by ELISA is as follows: Samples are centrifuged at 800×g for 15 minutes; 1 ml of the supernatant is added to 8 ml ice cold methanol and kept at −70° C. overnight to precipitate protein; and samples are then centrifuged at 800×g for 15 minutes, followed by a drying procedure in a Savant speed vac concentrator. The samples are reconstituted with 1 ml ice cold ELISA buffer and stored at −70° C. until assayed. The assay for eicosanoids (LTC$_4$ and 6-keto-PGF$_{1\alpha}$) is performed according to conventional ELISA procedures.

Compounds to be tested orally are suspended in 0.5% Tween 80. Compounds to be tested intraperitoneally are suspended in 0.5% methylcellulose in 0.9% saline.

The total metabolite level in lavage fluid/mouse is calculated and the significance is determined by a one-way analysis of variance with LSD comparisons to control (p≦0.05). Drug effects are expressed as a percent change from control values.

The activity of standard drugs in this assay is as follows:

| | $ED_{50}$ mg/kg p.o. | |
|---|---|---|
| Compound | $LTC_4$ | 6-keto-$PGF_{1\alpha}/TxB_2$ |
| BW755C | <10 | 22.0 |
| Phenidone | 24.0 | <30.0 |
| Indomethacin | Not Active | 0.126 |
| Ibuprofen | Not Active | 7.0 |

When tested in this assay a compound of the invention and the anti-inflammatory compound diclofenac gave the following results:

TABLE VI

| Compound of Example No. | Dose mg/kg | % Inhibition | | $ED_{50}$ | |
|---|---|---|---|---|---|
| | | $LTC_4$ | 6-keto-PGF | $LTC_4$ | 6-keto-PGF |
| diclofenac | | | | not active | 0.77 |
| 2 | 100 (p.o.)* | 78 | 65 | | |
| | 50 (p.o.) | 47 | −25** | | |

*perorally administered
**negative values denote potentiation.

The results show that unlike the drug diclofenac, whose anti-inflammatory activity arises by its inhibitory activity on the cyclooxygenase pathway, the compound of the invention exerts a potent inhibitory effect on both the lipoxygenase pathway and the cyclooxygenase pathway.

EXAMPLE 24

The $LTD_4$ antagonist activity of the compounds of the invention is assessed in the in vitro isolated guinea pig trachea assay.

This assay is carried out as follows:

Male Hartley guinea pigs (350–400 g) are euthanized by a blow to the head, the neck is opened and the trachea removed. The trachea is maintained in aerated physiological salt solution, cleared of connective tissue and fat and cut into rings approximately 2 mm in width (usually containing two cartilaginous segments per ring). Two pieces of silk suture are then passed through the lumen of the tracheal ring and are tied around the cartilage, one on each side of the trachealis muscle. The tracheal ring is suspended between a glass hook and a force displacement transducer in a 10 ml organ bath for measurement of isometric tension. Tissues are maintained at 37° C. in aerated (95% $CO_2$/5% $CO_2$) physiological salt solution of the following composition: NaCl(100 mM), $KH_2PO_4$ (1.18 mM), KCl (4.74 mM), $CaCl_2$ (2.5 mM), $MgSO_4 \cdot 7H_2O$ (1.19 mM), $NaHCO_3$ (25 mM), dextrose (11.1 mM) and indomethacin (1 $\mu$M). The tracheal rings are maintained at 2 g resting tension and equilibrated for 45 minutes (with frequent washing and readjustment of resting tension).

The tracheal rings are first contracted by the addition of carbachol ($3 \times 10^{-6}$M), to determine tissue responsiveness and establish a reference contraction. On attainment of a stable level of contraction (approximately 30 minutes), the tissues are washed several times until baseline tension has been restored and then re-equilibrated for 30 minutes. The tissues are then incubated for 45 minutes with a test antagonist (either $1 \times 10^{-6}$M or $1 \times 10^{-5}$M) or 10 $\mu$l of an appropriate solvent control (control, non-treated). One tissue in each group serves as the control. Twenty minutes prior to the construction of the $LTD_4$ cumulative concentration-response curve, L-cysteine ($1 \times 10^{-2}$M final bath concentration) is added to inhibit bioconversion of $LTD_4$ to $LTE_4$. Only one $LTD_4$ concentration-response curve is constructed in each tissue.

All responses to $LTD_4$ in an individual tissue are measured as a percentage of the reference contraction of that tissue to carbachol. $LTD_4$ antagonist activity is determined by comparison of the concentration response curves of $LTD_4$ in the presence and absence of antagonist. Assessment of the relative rightward shift of the antagonist treated curve relative to the solvent (control) treated tissue is calculated as a concentration ratio (Eq. A) and used in subsequent calculations to derive an antagonist $pK_B$ value (Eqs B and C). In the event that the maximum response to $LTD_4$ is depressed, the $EC_{50}$ for that particular curve is determined, an "apparent" $pK_B$ reported, and the compound reported as "not-competitive."

$$\text{Concentration Ration } (CR) = \frac{EC_{50} \text{ treated tissue}}{EC_{50} \text{ control}} \quad \text{A)}$$

$$K_B = \frac{[\text{Test Compound}]}{CR-1} \quad \text{B)}$$

$$-\log K_B = pK_B \quad \text{C)}$$

If a compound is found to be active and/or depress the maximal response to $LTD_4$, then a range of concentrations of the test compound should be used generating multiple concentration ratios which would then be used to perform a Schild analysis, and determination of a $pA_2$ value where appropriate.

The activity of reference leukotriene antagonists in this assay is as follows:

| Compound | $pK_B$ |
|---|---|
| Ly-171,883 | 7.44 ± 0.12 |
| Wy-48,252 | 6.90 ± 0.23 |

When tested in this assay, a compound of the invention gave the following results:

TABLE VII

| Compound of Example No. | $pK_B$ | Concentration Ratio (M) |
|---|---|---|
| 2 | 6.26 ± 0.4 | $1 \times 10^{-5}$ |

The above results demonstrate that the compound tested has significant leukotriene antagonist activity as measured in the in vitro isolated guinea pig trachea assay.

EXAMPLE 25

The compounds of the invention are further tested in the rat carrageenan paw edema assay to determine their ability to inhibit the acute inflammatory response.

This assay is carried out as follows:

140–180 gm Male Sprague-Dawley rats, in groups of 6 animals are injected subcutaneously in the right paw with 0.1 ml of 1% carrageenan at zero time. Mercury plethysmographic readings (ml) of the paw are made at zero time and 3 hours later. Test compounds are suspended or dissolved in 0.5% methylcellulose and given perorally 1 hour prior to carrageenan administration.

The increase in paw volume (edema in ml) produced by the carrageenan is measured. Paw edema is calculated (3 hour volume minus zero time volume), and percent inhibition of edema is determined. Unpaired Student's t-test is used to determine statistical significance.

The activity of standard drugs in this assay is as follows:

| Drug | Oral $ED_{50}$ (95% C.L.) mg/kg |
| --- | --- |
| Indomethacin | 3.7 (0.6, 23.8) |
| Aspirin | 145.4 (33.1, 645.6) |
| Phenylbutazone | 26.2 (2.3, 291.0) |

When tested in this assay, a compound of the invention and the anti-inflammatory drug diclofenac gave the following results:

TABLE VIII

| Compound of Example No. | Dose* (mg/kg) | % Inhibition 50 mg/kg (peroral) | $ED_{50}$ |
| --- | --- | --- | --- |
| diclofenac | 0.5 | 15 | 2.3 |
|  | 2.0 | 50 |  |
|  | 8.0 | 75 |  |
| 2 | 25 | 63 |  |
|  | 50 | 58 |  |
|  | 100 | 66 |  |

*administered perorally

The results show that the compound tested has significant activity in the rat carrageenan paw edema assay, evidencing an effect on the acute inflammatory response.

EXAMPLE 26

The compounds of the invention are tested in the rat acute gastroirritation assay to examine their potential for causing gastric irritation when administered at doses exceeding the effective dose. The nonsteroidal anti-inflammatory drug diclofenac is tested as a standard of a compound known to possess gastroirritant side effects.

This assay is carried out as follows:

Male Sprague Dawley rats (190–220 g) are fasted for 18 hours prior to drug administration. Rats are divided into groups of 8 and coded (i.e., observer of gastric lesions is not aware of drug treatment). Drugs are dissolved or suspended in 0.5% Tween 80 and administered by gastric intubation in a volume of 1 ml/100 g body weight, control rats receiving only Tween 80. Four hours after drug administration, rats are evaluated by recording the incidence and severity of gastroirritation using the following scoring system: 0) No irritation or lesions; 1) irritation (redness); 2) $\leq 5$ lesions (ulcers); and 3) >5 lesions. Dunnett's test ($\alpha = 0.05$) is used to calculate the mean $\pm SE$ of each test group and the statistical significance.

The results of this assay are presented in Table IX.

TABLE IX

| Compound of Example No. | Dose mg/kg | % of rats with GI lesions | $UD_{50}$ (mg/kg) |
| --- | --- | --- | --- |
| diclofenac |  |  | 20 |
| 2 | 400 | 0[1] |  |
|  | 200 | 0[2] |  |

[1] 6 Hours after single dose administration of compound.
[2] Result after 3 days of compound administration at indicated dose level.

The results show the tested compound of the invention to have no potential for acute gastroirritation when compared to diclofenac.

What is claimed is:

1. A compound having the formula

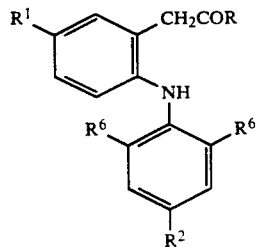

wherein
R is hydroxy, lower alkoxy or lower alkoxyamino;
$R^1$ is $A(CH_2)_nO$—;
$R^2$ is hydrogen;
n is 1–2;
A is a group having the formula

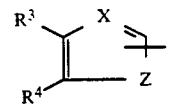

X is —N—;

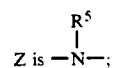

Z is —N—;

$R^3$ and $R^4$ taken together form a benzene ring;
$R^5$ is hydrogen or lower alkyl;
$R^6$ is hydrogen, halo or lower alkyl;
and the pharmacologically acceptable salts thereof.

2. The compound of claim 1, having the name 2-[(2,6-dichlorophenyl)amino]-5-[(1-methyl-1H-benzimidazol-2-yl)methoxy]benzene acetic acid methyl ester.

3. The compound of claim 1, having the name 2-[(2,6-dichlorophenyl)amino]-5-[(1-methyl-1H-benzimidazol-2-yl)methoxy]benzene acetic acid.

* * * * *